(12) United States Patent
Jimenez, Jr. et al.

(10) Patent No.: US 11,263,792 B1
(45) Date of Patent: Mar. 1, 2022

(54) CALIBRATION METHOD FOR A SPECTRAL COMPUTERIZED TOMOGRAPHY SYSTEM

(71) Applicant: National Technology & Engineering Solutions of Sandia, LLC, Albuquerque, NM (US)

(72) Inventors: Edward Steven Jimenez, Jr., Albuquerque, NM (US); Srivathsan Prabu Koundinyan, Highland Park, NJ (US); Isabel Gallegos, Albuquerque, NM (US); Adriana Stohn, Chandler, AZ (US); Gabriella Dalton, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/725,549

(22) Filed: Dec. 23, 2019

(51) Int. Cl.
*A61B 6/03* (2006.01)
*A61B 6/00* (2006.01)
(Continued)

(52) U.S. Cl.
CPC ............ *G06T 11/005* (2013.01); *A61B 6/032* (2013.01); *A61B 6/4085* (2013.01); *A61B 6/586* (2013.01);
(Continued)

(58) Field of Classification Search
CPC .............. G06T 11/005; G06T 11/006; G06T 2207/10081; G06T 2211/424; A61B 6/586; A61B 6/4085; A61B 6/032; G01N 23/046
See application file for complete search history.

(56) References Cited

U.S. PATENT DOCUMENTS 8,121,250 B2  2/2012 Dafni et al.
10,261,033 B2  4/2019 Jimenez, Jr. et al.
(Continued)

OTHER PUBLICATIONS

Chen, Y.-C., System Calibration and Image Reconstruction for a New Small-Animal Spect System, Doctoral Dissertation, The University of Arizona (2006) 315 pages.
(Continued)

*Primary Examiner* — Christine S. Kim
(74) *Attorney, Agent, or Firm* — Martin I. Finston

(57) ABSTRACT

A calibration method for an x-ray computerized tomography system and a method of tomographic reconstruction are provided. The calibration method includes steps of measuring at least one point spread function (PSF) at each of a plurality of points, compressing each PSF, and in one or more storing operations, storing the compressed PSFs in a computer-accessible storage medium. The PSF measurements are made in a grid of calibration points in a field of view (FOV) of the system. In the measuring step, an absorber is positioned at each of the calibration points, and an x-ray projection is taken at least once at each of those absorber positions. In the method of tomographic image reconstruction, projection data from an x-ray tomographic projection system are input to an iterative image reconstruction algorithm. The algorithm retrieves and utilizes a priori system information (APSI) The APSI comprises comprising point spread functions (PSFs) of all voxels in a voxelization of the field of view that are compressed in the form of vectors of parameters. For utilization, each retrieved vector of parameters is decompressed so as to generate a discretized PSF.

21 Claims, 12 Drawing Sheets

(51) Int. Cl.
*G01N 23/046* (2018.01)
*G06T 11/00* (2006.01)

(52) U.S. Cl.
CPC .......... *G01N 23/046* (2013.01); *G06T 11/006* (2013.01); *G06T 2207/10081* (2013.01); *G06T 2211/424* (2013.01)

(56) References Cited

U.S. PATENT DOCUMENTS

| | | | |
|---|---|---|---|
| 2016/0019678 A1* | 1/2016 | Cecil | G06T 5/003 382/132 |
| 2016/0316015 A1* | 10/2016 | Keating | G06T 11/005 |
| 2019/0219524 A1 | 7/2019 | Jimenez, Jr. et al. | |
| 2020/0240934 A1* | 7/2020 | Yl | G06T 7/70 |

OTHER PUBLICATIONS

De Man, B. et al., "An iterative Maximum-Likelihood Polychromatic Algorithm for CT," IEEE Transactions on Medical Imaging (2001) 20(10):999-1008.

Herman, G. T., "Correction for Beam Hardening in Computed Tomography," Phys. Med. Biol. (1979) 24(1):81-106.

Jimenez, E. S. et al., "Leveraging Multi-Channel X-Ray Detector Technology to Improve Quality Metrics for Industrial and Security Applications," Radiation Detectors in Medicine, Industry, and National Security XVIII, Grim, G. P. et al. (eds)., Proc. of SPIE (2017) 10393:103930G, 11 pages.

Panin, V. Y. et al., "Fully 3-D PET Reconstruction with System Matrix Derived from Point Source Measurements," IEEE Transactions on Medical Imaging (2006) 25(17):907-921.

Sato, T. et al., "Particle and Heavy Ion Transport code System, PHITS, version 2.52," Journal of Nuclear Science and Techology (2013) 50(9):913-923.

Yang, K. et al., "A geometric calibration method for cone beam CT systems," Med. Phys. (2006) 33(6):1695-1706.

Dalton, G. M. et al., "High-Fidelity Calibration and Characterization of a Hyperspectral Computed Tomography System," Sandia National Laboratories, Jul. 2019, SAND2019-7943C, 1 page.

Dalton, G. et al., "Virtual Testbed for Simulating Polychromatic Imagins Systems via PHITS," Sandia National Laboratories, Oct. 2019, SAND2019-12179A, 1 page.

Gallegos, I. O. et al., "High-Fidelity Calibration and Characterization of a Hyperspectral Computed Tomography System," Sandia National Laboratories, Aug. 2019, SAND2019-9617A, 1 page.

Gallegos, I. O. et al., "High-Fidelity Calibration and Characterization of a Hyperspectral Computed Tomography System," Sandia National Laboratories, Aug. 2019, SAND2019-9774A, 2 pages.

Gallegos, I. O. et al., "High-Fidelity Calibration and Characterization of a Hyperspectral Computed Tomography System," Sandia National Laboratories, Aug. 2019, SAND2019-9818C, 1 page.

Gallegos, I. O. et al., "High-Fidelity Calibration and Characterization of a Hyperspectral Computed Tomography System," Sandia National Laboratories, Aug. 2019, SAND2019-10201C, 30 pages.

Gallegos, I. O. et al., "High-Fidelity Calibration and Characterization of a Spectral Computed Tomography System," Sandia National Laboratories, Sep. 2019, SAND2019-10923C, 14 pages.

Jimenez, E. S., "High-Fidelity Calibration and Characterization of Hyperspectral Computed Tomography System," Sandia National Laboratories, Oct. 2019, SAND2019-11867, 38 pages.

* cited by examiner

CALIBRATION METHOD FOR A SPECTRAL COMPUTERIZED TOMOGRAPHY SYSTEM

ACKNOWLEDGEMENT OF GOVERNMENT SUPPORT

This invention was made with Government support under Contract No. DE-NA0003525 awarded by the United States Department of Energy/National Nuclear Security Administration. The Government has certain rights in the invention.

FIELD OF THE INVENTION

The invention relates to computerized tomography, and more particularly to methods for calibrating computerized x-ray tomography systems.

ART BACKGROUND

Computerized tomography (CT) is a technique for reconstructing three-dimensional visualizations of objects from scans obtained using x-rays or other penetrating radiation. CT has been a valuable tool for many years in industry, medicine, and other fields.

One of the underlying principles of CT is the Lambert-Beer law, which describes the attenuation of radiation as it passes through a body. For a beam of radiation of initial intensity $I_0$ that traverses a uniform body of attenuation coefficient $\mu$, the Lambert-Beer law predicts a final intensity $I = I_0 e^{-\mu x}$, where x is the path length through the body. In other words, $-\ln I/I_0 = \mu x$. If the beam traverses a sequence of bodies of respective attenuation coefficients $\mu_1, \mu_2, \ldots, \mu_N$ and respective path lengths $x_1, x_2, \ldots, x_N$, then $-\ln$ $$I/I_0 = \sum_{i=1}^{N} \mu_i x_i.$$

It should be noted that in the present discussion, it is assumed that the attenuation coefficients $\mu_i$ are independent of beam energy $\kappa$. In more general cases they may be represented by expressions of the form $\mu_i(\kappa)$ to explicitly indicate energy dependence.

A planar section of a three-dimensional body may be subdivided into a large number of individual volume elements, or "voxels". For purposes of the present discussion, it is assumed that each voxel is small enough that it can be regarded as uniform in its attenuation coefficient, and it is assumed that if a beam traverses a voxel, every part of the beam sees the same path length through the voxel. Under those assumptions, and assuming that the path length $x_i$ is known for each voxel, the attenuation expression $-\ln$ $$I/I_0 = \sum_{i=1}^{N} \mu_i x_i$$

for any beam that traverses the planar section can be regarded as a linear equation in the variables $\mu_i$.

In a typical CT scan, the radiation source and the detector array are symmetrically placed on diametrically opposing sides of a rotational axis, referred to as the "isocenter". The object to be scanned is placed between the source and the detector. Between exposures, the angular position of source and detector about the isocenter is advanced in increments. Each exposure is recorded by the detector array. The detector array contains a plurality of detector elements, distributed in one or two dimensions, that produce a discrete spatial sampling of the projected image. Some projections, for example "fan beam" projections, are sampled in only one dimension, that is, they are sampled by a linear array of detector elements. Other projections, such as "cone beam" projections, are sampled in two dimensions. One-dimensional sampling will be assumed in the present discussion. Accordingly, only a single planar section of the object is projected.

Under the above assumptions, a projection will produce a vector of outputs from the respective detector elements. Each element of that vector corresponds to a respective path through the object, and each of these elements can be mapped to an attenuation value $-\ln I/I_0$ corresponding to the respective path.

If enough projections are taken (i.e., if the angular increments are small enough), scanning through a complete angular range will provide attenuation values for paths passing through all of the voxels of the object. A complete angular range is typically 180°, although for some purposes a full circle may be preferred.

A system of linear equations of the form $$\sum_{i=1}^{N_j} \mu_{ij} x_{ij} = -\ln I_j/I_0$$

can be assembled, in which the index j ranges over all of the paths in all of the projections, and in which the value on the right-hand side of each equation is known from measurements. In principle, such a system of equations can be solved to find the values of the attenuation coefficients for the respective voxels. In practice, approximation techniques are generally used, not least because the system of equations is typically overdetermined.

An image of the projected planar section can be reconstructed from the attenuation values, and by repeating the process over many planar sections, a three-dimensional image of the object can be reconstructed. Generally, there is an underlying assumption that each of the attenuation coefficients $\alpha_{ij}$ is constant. In practice, the reconstructed image will often contain artifacts due to the failure of this assumption, as well as to other deviations from ideality. An artifact, in this regard, is an image error that is propagated by the reconstruction process. Example artifacts include spurious streaks, arcs, and shading.

The linear algebraic treatment outlined above is useful, in a pedagogical sense, for introducing the conceptual underpinnings of CT. However, other algorithmic treatments have been more successful in practice for producing high-quality reconstructions. For example, one widely used class of algorithms is filtered back-projection.

One of the theoretical foundations of filtered back-projection is the Fourier Slice Theorem. The Fourier Slice Theorem expresses a relationship between the object (in planar section) and the measured output of the scan using the Fourier transform. In this regard, the conjugate variables that are related through the Fourier transform are spatial position and spatial frequency. Accordingly, if O denotes the object, then O' denotes its conjugate, where O' is the two-dimensional Fourier transform of O.

As explained above, a scan is constituted by a sequence of projections taken at successive angular positions. According to the Fourier Slice Theorem, the one-dimensional Fourier transform of each scan is equivalent to a linear section though O', taken at an angle corresponding to the rotational position of the scan. Various well-known algorithms apply this result in reconstructing the object from the scan.

In filtered back-projection, a sinogram is taken as input. A reverse transformation is applied to map the sinogram back to a reconstructed object. Numerical filtering is included, which among other things compensates for the undersampling of higher spatial frequencies. A sinogram is a composite image assembled by stacking each horizontally displayed projection above the preceding projection in a vertical sequence. Filtered back-projection algorithms and various other types of reconstruction algorithms are well-known in the art and need not be described here in detail.

A naïve application of the above techniques relies on the linearity of the system (i.e. the scanning system together with the scanned object) for accurate reconstruction. Roughly speaking, the system is linear if the Lambert-Beer law holds identically for all wavelengths, and if identical voxels evoke identical detector responses irrespective of where they are located within the sample object.

Real systems deviate from linearity in various ways. These deviations, if uncorrected, can produce artifacts in the reconstructed image. Some nonlinearities are due to imperfections in the scanning system, such as mechanical misalignment. Others are due to detector imperfections and nonideal detector behavior. For example, manufacturing variability and drift in dark current might cause different detector elements to have different levels of sensitivity. In another example, the detector response might vary nonlinearly with the intensity of the detected radiation.

Calibration data can be used to correct for some of these nonlinearities, at least in part. For example, the results of an air scan, i.e. a scan of an empty sample chamber, can be used to correct for differences in detector response. Shielding the detectors with an absorber of known attenuation, and varying the absorber thickness, can be used to measure the detector response as a function of radiation intensity.

Other nonlinearities arise when there is a failure in the assumption that the attenuation coefficients $\alpha$ are constant. For example, beam hardening produces nonlinearities of that kind. Conventional x-ray CT generally uses radiation beams with a substantial content of bremsstrahlung, which is spectrally broadband and continuous. The spectral content can change as the less penetrating (generally, the lower-energy) wavelengths are absorbed or scattered along a path through the object. Downstream objects on a given path will therefore exhibit weaker effective attenuation than they would if they were located further upstream on the same path. The resulting error can be compounded in the detector if the detector response is wavelength-dependent.

Some numerical compensation for beam hardening is possible, but it is generally inadequate because it relies on a priori assumptions about the composition of the sample object. A more direct approach is to limit the scan to a narrow spectral window through filtering or through energy-selective detection.

As explained above, calibration data can be used in various ways to compensate for some of the imperfections in the scanning system that produce artifacts in the reconstructed image. Calibration data are also used more generally for characterizing the scanning system. Often, a sample object having known properties is scanned in a calibration procedure. Such an object is referred to as a phantom. A common example of a phantom is a plastic cylinder filled with water.

One of the important properties of a scanning system is its point spread function. The point spread function is the image of a small absorber, or "point source", as projected onto the detector array. In practice, the point spread function can be measured from the projected image of, e.g., a metal bead, a metal wire, a small hole in an absorptive plate, or the edge of a metal plate.

Those skilled in the art will recognize that the point spread function is the impulse response of the system, where the impulse is provided by the small feature that is projected. The point spread function is a factor in determining the spatial resolution of the scanner.

As those skilled in the art will also recognize, the Fourier transform of the point spread function is the modulation transfer function (MTF) of the scanner.

As noted above, limiting the spectral bandwidth of the scanning beam can be useful for mitigating the nonlinearities due to beam hardening. Band limiting is useful for other purposes as well, such as discrimination of unknown materials. That is, each material component of an object scanned, e.g., by x-rays, has a characteristic x-attenuation spectrum for the scanning radiation. Hence when images of the object are reconstructed from data taken in different band-limited energy channels, each different material component will potentially exhibit a different attenuation profile. The attenuation profile describes how the contrast value of a material component varies from channel to channel in the reconstructed images. Images taken in only a few different energy channels could be sufficient to distinguish material components, if enough of their respective attenuation profiles has been revealed.

For the above reasons, among others, multispectral CT imaging has useful applications. In this regard, multispectral imaging means imaging of the same object in more than one energy channel.

It is useful to characterize a linear CT imaging system by a discrete-to-discrete system operator (also sometimes referred to as a "system matrix", particularly if it is stored as a numerical array) that relates discrete object points to discrete pixel values in the image. A system operator can be compiled from measurements taken from point sources within the field of view (FOV) of the instrument. Such a system operator is useful, e.g., in calibration and in image reconstruction. It is more difficult to characterize the imaging system, however, when the assumption of linearity does not hold.

Some discrete-to-discrete system operators, compiled from point-source measurements, have been reported in the technical literature. For example, Y. C. Chen, "System Calibration and Image Reconstruction for a New Small-Animal SPECT System," *Doctoral Dissertation*, The University of Arizona (2006) (hereinafter, "Chen 2006)", reports on an estimated linear, discrete-to-discrete system operator for single-photon emission computerized tomography (SPECT). The entirety of Chen 2006 is hereby incorporated herein by reference.

In SPECT, an object is made radioactive by labeling it with gamma-emitting radionuclides. The emitted gamma rays are detected, and the detector responses are combined to form a projected image. To acquire enough projected images for a tomographic reconstruction, it is typical in SPECT systems to mount a collimated detector array on a moveable platform that is rotated about the object during a scan, while multiple projections are taken.

Similarly, V. Y. Panin, F. Kehren, C. Michel, and M. Casey, "Fully 3-d pet reconstruction with system matrix derived from point source measurements," *IEEE Transactions on Medical Imaging,* 25(7) (2006) 907-921 (hereinafter, "Panin 2006"), reports on an estimated linear, discrete-to-discrete system operator for positron-emission tomography (PET). The entirety of Panin 2006 is hereby incorporated herein by reference.

In Chen 2006 and Panin 2006, single-energy gamma rays were emitted to measure narrow sets of materials in the FOV of the instrument. In both works, the system operator was assumed to be linear.

To obtain the greatest benefit from multispectral imaging, there is a need for new ways to characterize the imaging system that account for system nonlinearities and that are particularly suited to multispectral x-ray image analysis and reconstruction.

SUMMARY OF THE INVENTION

We simulated a multispectral computerized tomography (H-CT) system using a Monte Carlo radiation and electron particle simulator to generate large volumes of data representative of the imaging output of a real-world H-CT system. Our studies confirmed that it is feasible to estimate the nonlinear system operator of a H-CT system as a sequence of linear operators.

The system matrix was constructed explicitly from the point response functions of small objects ("sources") situated at discrete points in the object space, within the field-of-view of the instrument. These point response functions were generated analytically or by simulation.

The point response functions were parametrized by a basis function so that they could be stored in compressed form while preserving knowledge of the system characteristics and decompressed as needed. To overcome limitations of spatial resolution, an extrapolation method was used to estimate the point-spread functions of sub-millimeter sources in the object space. An interpolation method was used to reduce the number of scans needed for full system characterization.

To confirm that essential information was preserved in the compression of the system operator, we used the compressed system operator to reconstruct the object from a sinogram. The reconstruction was performed using a Maximum-Likelihood Expectation-Maximization (MLEM) reconstruction algorithm.

A massively parallel computing environment was needed to make the task of reconstruction tractable, because a decompression of point-response data needed to be performed each time an entry in the system operator was extracted.

We performed the reconstruction on a Nvidia Titan V graphics processing unit. An example reconstruction took approximately seventy-two hours to complete. An accurate reconstruction was confirmed.

Accordingly, the invention in a first aspect relates to a calibration method for an x-ray computerized tomography system including steps of measuring at least one point spread function (PSF) at each of a plurality of points, compressing each PSF, and in one or more storing operations, storing the compressed PSFs in a computer-accessible storage medium. The PSF measurements are made in a grid of calibration points in a field of view (FOV) of the system. In the measuring step, an absorber is positioned at each of the calibration points, and an x-ray projection is taken at least once at each of those absorber positions.

In embodiments, respective PSFs are measured at the calibration points in a plurality of x-ray energy bins.

In embodiments, the PSFs are compressed by fitting each PSF to an ellipse spline. Each compressed PSF may consist, e.g., of at most four parameters of the spline fit. In these and other embodiments, each compressed PSF may be represented by, e.g., a vector of parameters including a scale parameter, a translational parameter, and at least one shape parameter.

In embodiments, the measuring step comprises performing a scan at each calibration point, each scan comprising multiple x-ray projections taken over a range of projection angles.

In embodiments, the measuring of a PSF comprises projecting two or more absorbers having different radii so as to generate a graduated set of two or more respective projections, and the compressing of a PSF comprises extrapolating parameter values from its graduated set of projections.

In embodiments, imputed PSFs are calculated for points in the FOV that are additional to the calibration points by interpolating measured PSFs. The imputed PSFs are stored in compressed form.

In embodiments, the compressed PSFs are stored in a matrix of entries arranged in rows and columns, in which each entry corresponds to a vector of parameter values representing a respective compressed PSF.

The invention in a second aspect relates to a method of tomographic image reconstruction, in which projection data is provided, e.g. in the form of one or more sinograms, as input to an iterative image reconstruction algorithm resident on a digital processing device. The projection data are a product of an x-ray tomographic projection system having a field of view (FOV). The running of the algorithm comprises retrieving a priori system information (APSI) from a computer-accessible storage medium and utilizing the retrieved APSI. The APSI comprises point spread functions (PSFs) of all voxels in a voxelization of the field of view. Each retrieved PSF is retrieved in the form of a vector of parameters. To utilize the APSI, each retrieved vector of parameters is decompressed so as to generate a discretized PSF.

In embodiments, the APSI comprises a scan for each voxel in the voxelization of the field of view, and each scan comprises multiple PSFs corresponding to a range of projection angles.

BRIEF DESCRIPTION OF THE DRAWINGS

FIG. 6A is a graph of the parameter $a_L$, with line of best fit indicated. FIG. 6B is a graph of the parameter $a_R$, with line of best fit indicated. In the illustrated example, the projections are taken at position (5,165) in the FOV. Values were calculated using ideal H-CT data.

FIG. 7A is a graph of parameter b versus radius, with line of best fit indicated, at position (5,165) in the FOV. FIG. 7B is a graph of parameter $x_0$ versus radius at position (5,165) in the FOV. Values were calculated using ideal H-CT data.

DETAILED DESCRIPTION

Figure 1:
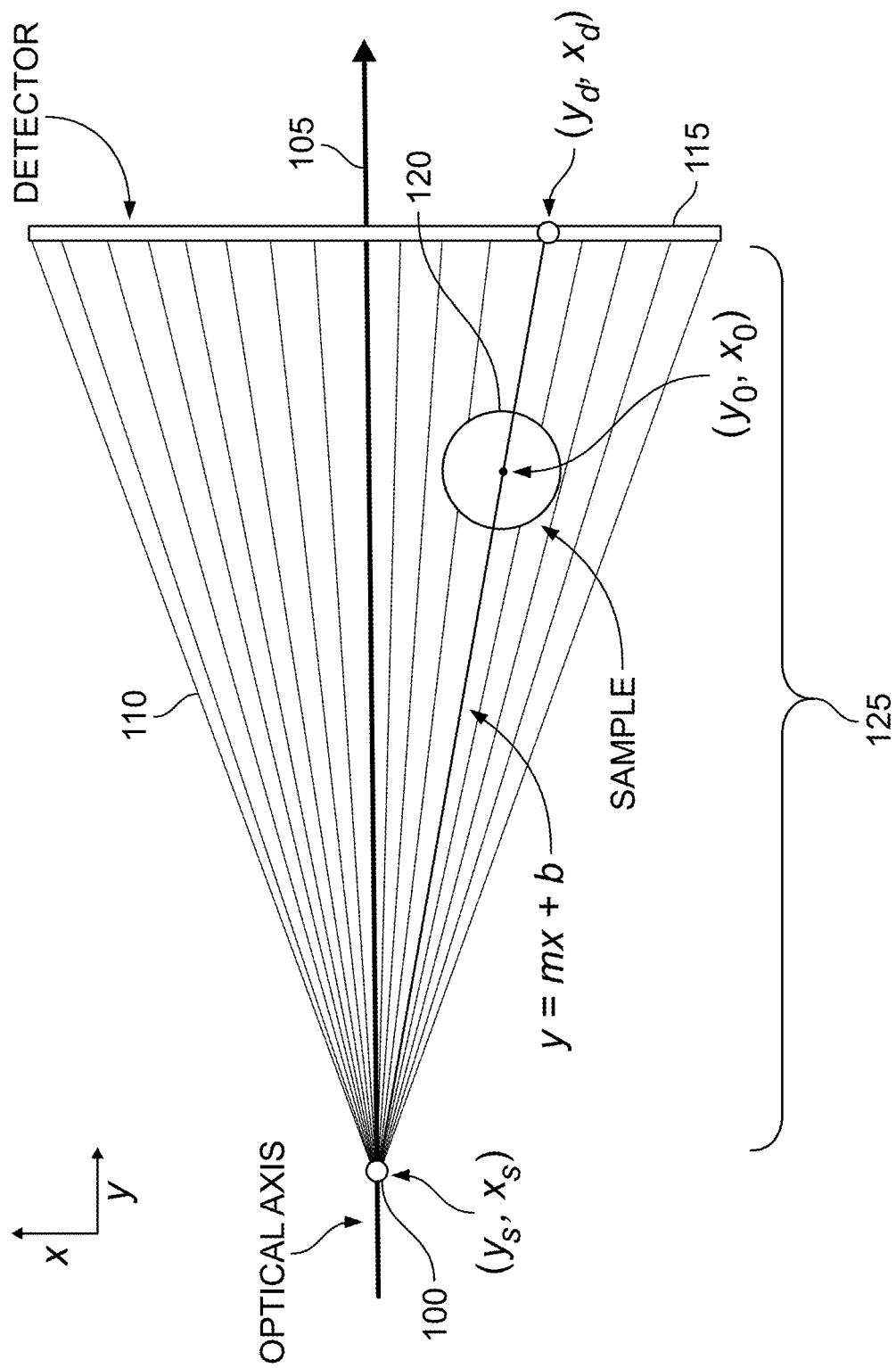
FIG. 1 is an idealized sketch of the system geometry for an H-CT instrument.

A typical projection system is schematically illustrated in plan view in FIG. 1. As shown in the figure, the x-ray source 100 is situated on the optical axis 105 of the system and emits a fan beam or cone beam 110 toward the detector array 115. A single, cylindrical absorber 120 is shown as positioned within the field-of-view (FOV) 125 of the system.

Figure 2:
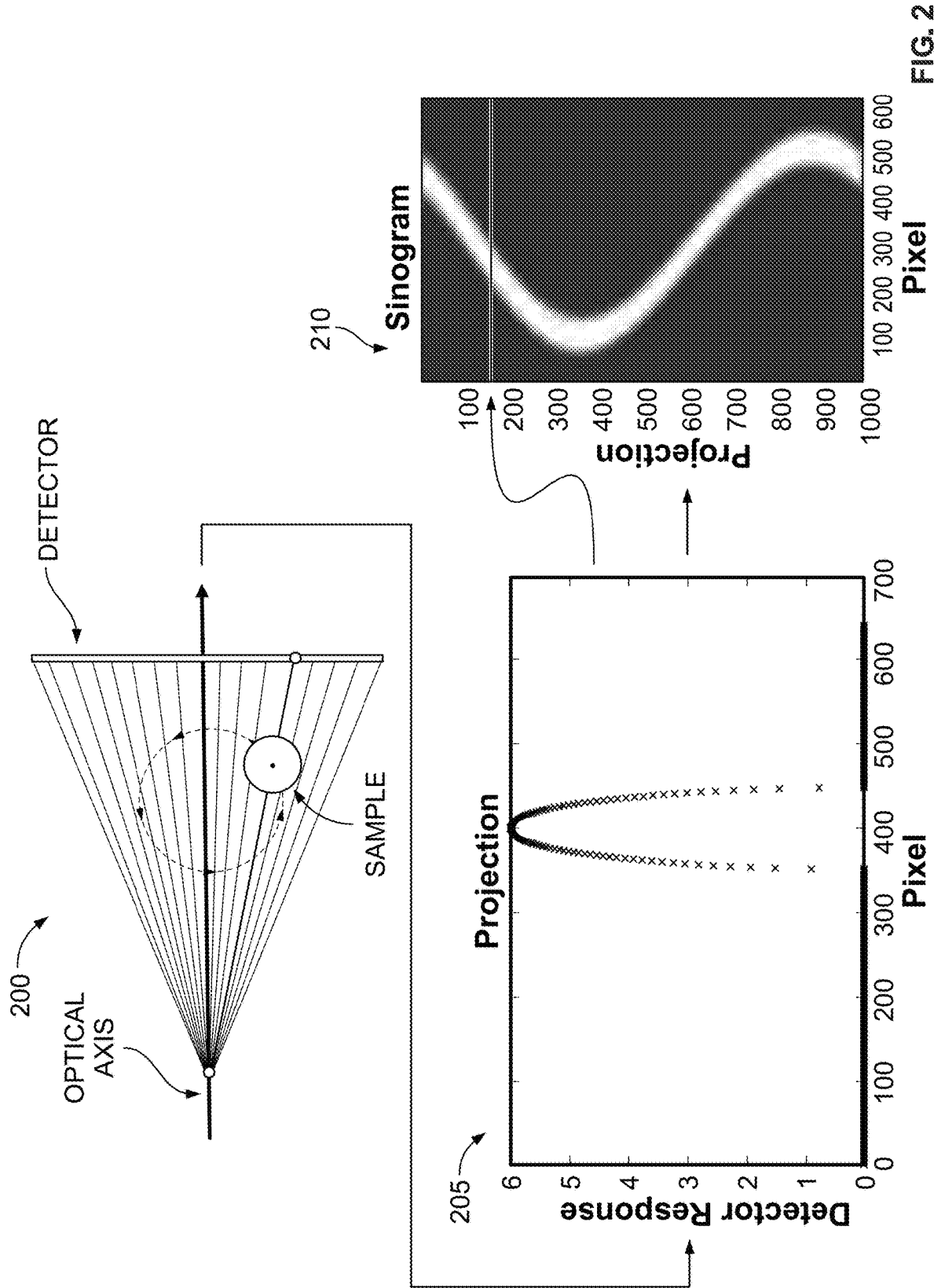
FIG. 2 illustrates an example process for creating a projection of a single cylinder in the field-of-view of an H-CT instrument.

FIG. 2 illustrates how a scan of absorber 120, using the projection system of FIG. 1, is used to create a sinogram. In view 200, one projection is shown. The projection is taking place at a projection angle represented by the angle subtended between the optical axis and the ray drawn from the x-ray source through the center of the cylindrical absorber.

The pixel values measured by the detector array (which in this example is assumed to be a linear array of detector elements) are plotted, as shown in view 205, as response versus position in the detector array. As shown in view 210, the resulting profile is also graphed, as intensity versus position, in a corresponding row of the sinogram. Many such projections are taken at successive increments of the projection angle. The relative rotations between the x-ray source and the FOV as the projection angle is incremented are indicated symbolically in FIG. 2 by a circulating arrow.

The projection at each respective projection angle adds a corresponding row to the sinogram. Thus, the complete sinogram is a record of a full scan of the object in the FOV. In a multispectral (H-CT) system, energy discrimination is possible, and accordingly, the detector responses are recorded separately for different energy bins. Consequently, an H-CT system can create a set of multiple sinograms for respective energy bins.

We based our simulation on an experimental H-CT system that is in use in our laboratory. It is the high-energy spectral x-ray computed tomography system described in Edward S. Jimenez et al., "Leveraging multi-channel x-ray detector technology to improve quality metrics for industrial and security applications," *Radiation Detectors in Medicine, Industry, and National Security XVIII*, volume 10393, International Society for Optics and Photonics (2017), page 103930G, the entirety of which is hereby incorporated herein by reference.

Our laboratory system includes a Comet x-ray source and a detector composed of five customized Multix ME100 modules. The source is a bremsstrahlung source that emits a distribution of energies with a maximum beam energy of 450 keV. This relatively high energy is desirable because it increases penetration and because it reduces artifacts, relative to more conventional lower-energy Bremsstrahlung sources. The source has a high flux capability, which enhances the signal-to-noise ratio.

The detector is a linear array of 640 pixels calibrated for 300 keV across 128 energy channels. The detector produces energy-resolved data, so that when an x-ray photon strikes a pixel of the detector, the photon is binned into one of the 128 channels according to its energy. The attenuation data is accordingly spatially resolved in each of the 128 energy channels. The source-to-detector distance is approximately 2.05 meters, and the object-to-detector distance is variable.

The system has a 500-mm field of view (FOV) and 640×640 voxel slices with a 0.8-mm pixel pitch.

In traditional systems, the individual photon energies cannot be determined or resolved. Hence, each voxel in a reconstructed scan has associated with it only a single photon count or other radiographic exposure value that is cumulative across the energy spectrum. Another drawback in traditional systems is that artifacts are more prevalent because of beam hardening by high-density materials, among other factors. Using a multichannel CT system helps to overcome these problems and, in addition, it provides spectral data, not otherwise obtainable, that can be used for material identification.

The simulated tool that we used was the Particle and Heavy Ion Transport code System (PHITS), a Monte Carlo radiation and electron particle simulator developed by the Japanese Atomic Energy Agency (JAEA).

The numerical simulation was able to emulate non-idealities such as noise effects and bremsstrahlung-induced streaking artifacts. This gave us greater confidence that its predictions would apply accurately to real-life implementations.

The imaging system. A digital imaging system can be modeled as a mapping from an object to an image, in which the object is conceptualized as a function of continuous variables and the image is a set of discrete measurements. In these terms, the true H-CT system (in other words, the real-life system that is approximated through modeling) can be represented by the continuous-to-discrete operator H in the following expression:

$$\vec{g} = Hf + \vec{n}.$$

In the above expression, f is the continuous object, $\vec{g}$ is the discretized image containing pixel information, and $\vec{n}$ is the system noise.

If the image is distributed across a linear array of pixels and the object is discretized into an array of n voxels that is flattened into a linear sequence, we can approximate the linear H-CT system in terms of an m×n discrete-to-discrete linear imaging system operator H according to the following expression:

$$\vec{g} = H\vec{f} + \vec{n}.$$

In the above expression, $\vec{f}$ is the discretized n×1 approximation of the object, and $\vec{g}$ and $\vec{n}$ have dimensions m×1. The dimension m is the number of pixels, multiplied by the total number of projections.

Figure 3:
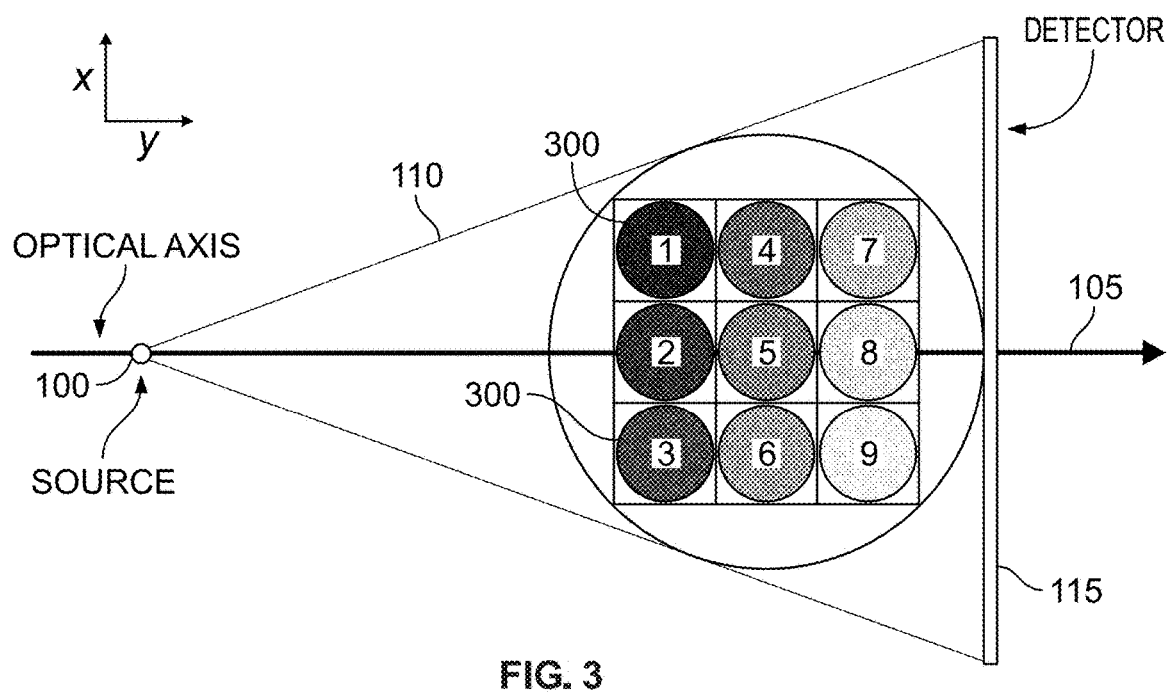
FIG. 3 is an idealized sketch showing nine cylinders distributed in the field-of-view of an H-CT instrument.

The system operator. In order for the approximated system operator H to map from a discrete object space to a discrete image space, the continuous FOV of the instrument must be discretized into a set of n points. To quantify the point response function for each point in the object space, we represented each point by one of n identical cylindrical absorbers, referred to below simply as "cylinders". The cylinder radius was approximately equal to the system's pixel pitch. An example of how cylinders 300 can be distributed in the FOV is provided in FIG. 3, where like reference numerals call out features previously discussed with reference to FIG. 1.

As those skilled in the art will understand, modeling an imaging system with a two-dimensional detector array would call for three-dimensional absorbers such as x-ray absorbing spheres. However, the detector array in the model described here is a linear array. For that purpose, the dimensionality of the absorber can be reduced to that of a cylinder. Similarly, the projection beam of x-rays that we envisage in example implementations with a two-dimensional detector array is a cone beam. But for purposes of the modeling discussed here, the dimensionality is reduced to that of a fan beam.

As noted above, the encoding operator H is an m×n matrix, in which m is the total number of pixels in the detector multiplied by the number of projections. The dimension n is the number of cylinders in the FOV. Within the FOV, the cylinders are physically distributed in a two-dimensional array. To create the encoding operator, however, the cylinders are serially numbered from 1 to n. Each column of the system matrix corresponds to a flattened sinogram of a respective one of the cylinders in the FOV.

For practical applications, a massive volume of data would have to be encoded in the system operator, making data storage a significant challenge. By way of illustration, a current state-of-the-art single-channel CT system with a large detector array could generate as much as 6 TB of data, or even more, per scan. For such a system, the storage requirement for a full three-dimensional calibration at high resolution could reach several yottabytes per energy channel.

To solve the problem of prohibitive storage requirements, we developed a compression method that reduces the size of the model to the scale of hundreds of GB.

To ensure the accuracy of our calibration measurements, we took projection data based on cylinders of practical size (generally, radii of one millimeter or more), and applied an extrapolation technique to estimate projection data for (imputed) concentrically located cylinders with submillimeter radii.

Because of the time required for each scan and the large number of cylinders, it would be very time-consuming to explicitly measure projection information from the complete set of sources in the FOV. To reduce the time required while still maintaining a sufficiently fine sampling of the FOV, we projected a subsampling of the cylinders and applied an interpolation method to calculate projection data for imputed cylinders at additional spatial positions. (By "imputed cylinder" we mean a cylinder that is mathematically represented in our computational model irrespective of whether it has a counterpart in a physical implementation of the modeled system.)

We found that our compression, extrapolation, and interpolation methods were helpful in creating a system operator that could be used in tractable computations. In particular, we found that we could manage H-CT data accurately and efficiently by compressing the system operator for storage, and then using analytic methods to decompress it for application to an object vector $\vec{f}$.

It should be understood that in the work described here, the system operator H was generated from simulated data, and not from experimental measurements. Thus, the projection data were not taken on a physical implementation of the H-CT system. As mentioned above, rather, the projection data were produced by PHITS, a Monte Carlo radiation and electron particle simulator. Below, we refer to the data produced by the Monte Carlo code as "synthetic data".

The Monte Carlo simulation had some realistic aspects; for example, it included the effects of Poisson noise and downscatter noise. Poisson noise is statistical noise due to the discrete nature of detected photons. Downscatter noise occurs when inelastic scattering (due to Compton scattering and the photoelectric effect) causes x-ray photons to lose energy before they are counted.

However, the simulation did not include the effects of other types of detector noise, such as electronic readout noise, pulse pileup (in which photon coincidences at the detector are counted as a single, higher-energy photon), and corrupted photon counts due to detector thermal fluctuations. Defective pixels in the detector can also contribute noise, but this was also omitted from the simulation.

The simulation also assumed ideal geometry, i.e., perfect alignment of the projection system. However, it should be noted that misalignments in a physical projection system are measurable and can be included in a simulation, if desired.

We envisage practical applications in which the point-by-point scans of sources in the FOV are used to construct the system operator of a physically implemented H-CT system.

Knowledge of the system operator is then used for purposes of calibration and image reconstruction. The point source to be scanned is a millimeter-scale spherical bead of a suitable x-ray absorber material such as copper, tungsten, or lead. The absorber material is chosen to be neither completely transparent nor completely opaque in the x-ray energy range of interest, given the absorber thickness.

A precision positioner can be used for placement of the point source at designated grid positions within the FOV for each scan. If necessary, the point source can be supported using materials and thicknesses that are effectively x-ray transparent at the energies of interest, such as thin polymeric materials. It is also worthy of note that data compression and decompression can possibly mitigate artifacts added to the scan by positioning hardware. For example, it could be possible to model such artifacts with one or more extra data-compression parameters that are excluded in the subsequent data decompression.

In practice, it may be desirable to recalibrate a real-life H-CT system by repeating the point-by-point scan at suitable intervals such as six-month intervals.

Compression of the system operator. Each projection is represented by an n×1 vector, where n is the number of pixels in the detector. To compress each projection, each projection is fitted to a basis function so that it can be represented using only the small set of parameters that characterize the basis function.

Known optimization methods can be used to find the best fit of the projection data. For example, we used the Nelder-Mead method, which is a well-known numerical method that seeks the maximum or minimum of an objective function in a multidimensional space by direct search.

The Nelder-Mead method was chosen because it can find a best fit even when the derivative does not exist at every point. Also, because the Nelder-Mead method works well with noisy data, it was especially useful for treating the simulated data produced by PHITS and would likewise be useful for treating real-world H-CT data.

Although other basis functions may be suitable, our currently preferred basis function is an ellipse spline given by the following expressions:

$$y_L = \left(\frac{a_L^2 - (x - x_0)^2}{a_L^2}\right)^{1/2} \cdot b, \; x < x_0$$

$$y_R = \left(\frac{a_R^2 - (x - x_0)^2}{a_R^2}\right)^{1/2} \cdot b, \; x \geq x_0$$

As those skilled in the art will understand from the above expressions, our basis function is defined piecewise by two ellipses (i.e., a "left-hand" ellipse L and a "right-hand" ellipse R) and the four parameters $a_L$, $a_R$, b, and $x_0$.

The parameters parameters $a_L$ and $a_R$ may more generally be viewed as special cases of shape parameters. Likewise, the parameter b may be more generally viewed as a special case of a scale parameter, and the parameter $x_0$ may be more generally viewed as a special case of a translational parameter. Variations of our approach in which other choices for parameters of these types are used will be apparent to those skilled in the art and should be understood as falling within scope of the present invention.

More generally, the parameters for the ellipse spline are indexed as $a_L^{\mu\kappa}$, $a_R^{\mu\kappa}$, $b^{\mu\kappa}$, and $x_0^{\mu\kappa}$, where $\mu$ and $\kappa$ are the respective indices for the projection ($\mu=1, \ldots, m$) and for the cylinder in object space ($\kappa=1, \ldots, k$). The parameters are stored in an m×n×k matrix, where n is the total number of parameters required for each spline (n=4 in the current example).

In performing the Nelder-Mead optimization, the parameter values are subject to the following constraints: (1) the $a_L^{\mu\kappa}$ and $a_R^{\mu\kappa}$ must be positive and they must be contained in the pixel domain as defined by the pixels on the detector; and (2) the parameters $x_0^{\mu\kappa}$ must be contained in the pixel domain.

Figure 4:
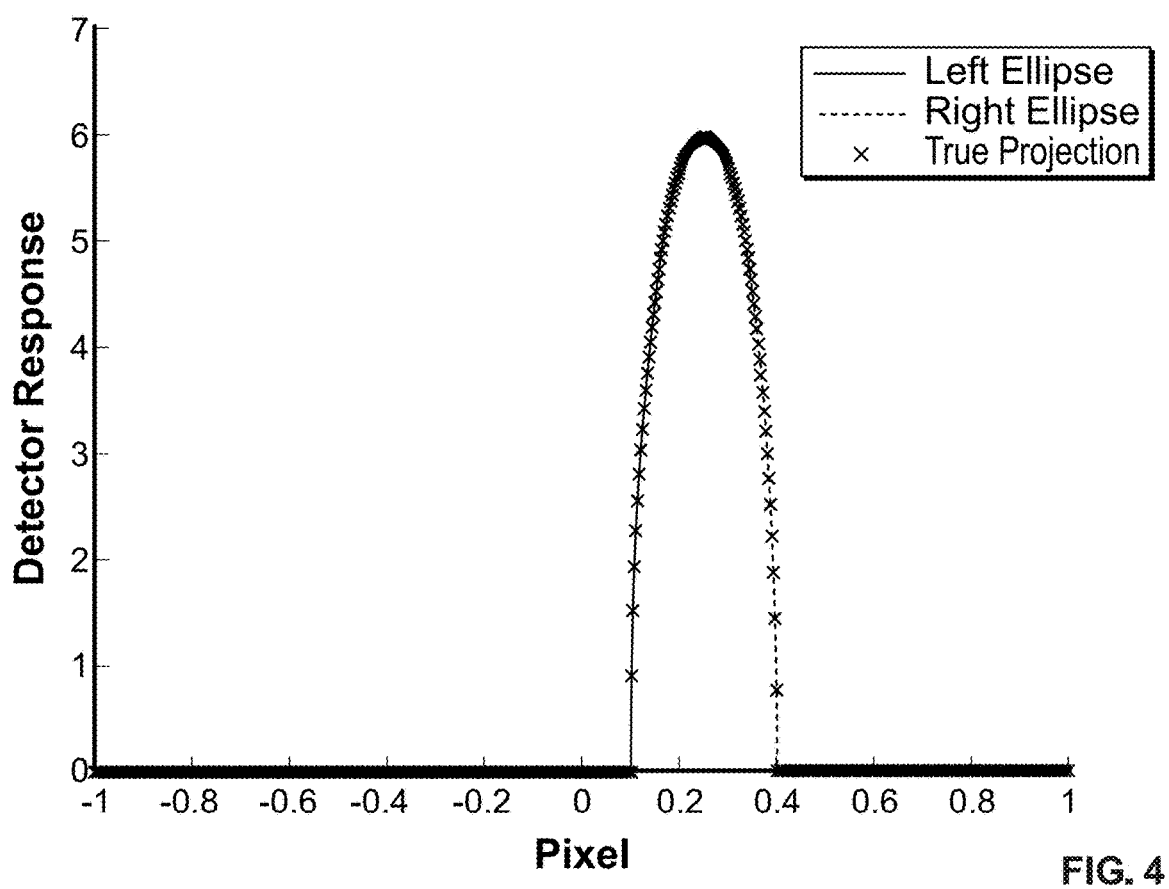
FIG. 4 is a graphical example of how an ellipse spline can be fitted to projection data.

FIG. 4 shows the ellipse spline fit for a representative cylinder of 3-cm radius in the FOV. The Nelder-Mead error is defined as the norm of the difference between the true projection and the fitted basis function. Using ideal H-CT data, we calculated a mean error over nine cylinders arrayed in the FOV was $2.30 \times 10^{-3}$, and a standard deviation of $8.15 \times 10^{-4}$. By "ideal" data we mean analytically generated data assuming a constant, energy-independent attenuation coefficient and a noise-free imaging system.

To fully calibrate the H-CT system, the point-response function must be measured at the system's resolution at every location in the FOV. As a practical matter, we approximate the point-response functions over a continuous FOV by sampling, in each of a plurality of discrete voxels, a cylinder whose radius is approximately equal to the system's resolution. This problem presents two challenges: (1) measuring the point-response function at submillimeter resolution, and (2) sampling every point of interest in the FOV. A parameter-extrapolation method, described below, addresses the first of these problems. A system-operator interpolation method, also described below, addresses the second of these problems. are presented below.

Extrapolation of parameters. CT scans to measure the point response functions of objects at or below the system resolution (generally, submillimeter objects) are subject to inaccuracy due to insufficient attenuation. Instead of attempting these measurements directly, we estimated the projection data of submillimeter cylinders using an extrapolation technique. That is, by extrapolating projections of cylinders of larger radii centered on the same point in the FOV, we believe that we can accurately approximate the projection of a cylinder of smaller radius. In carrying out this technique, we found it unnecessary to extrapolate each full projection. Instead, we extrapolated the parameters $a_L$, $a_R$, b, and $x_0$.

Figure 5:
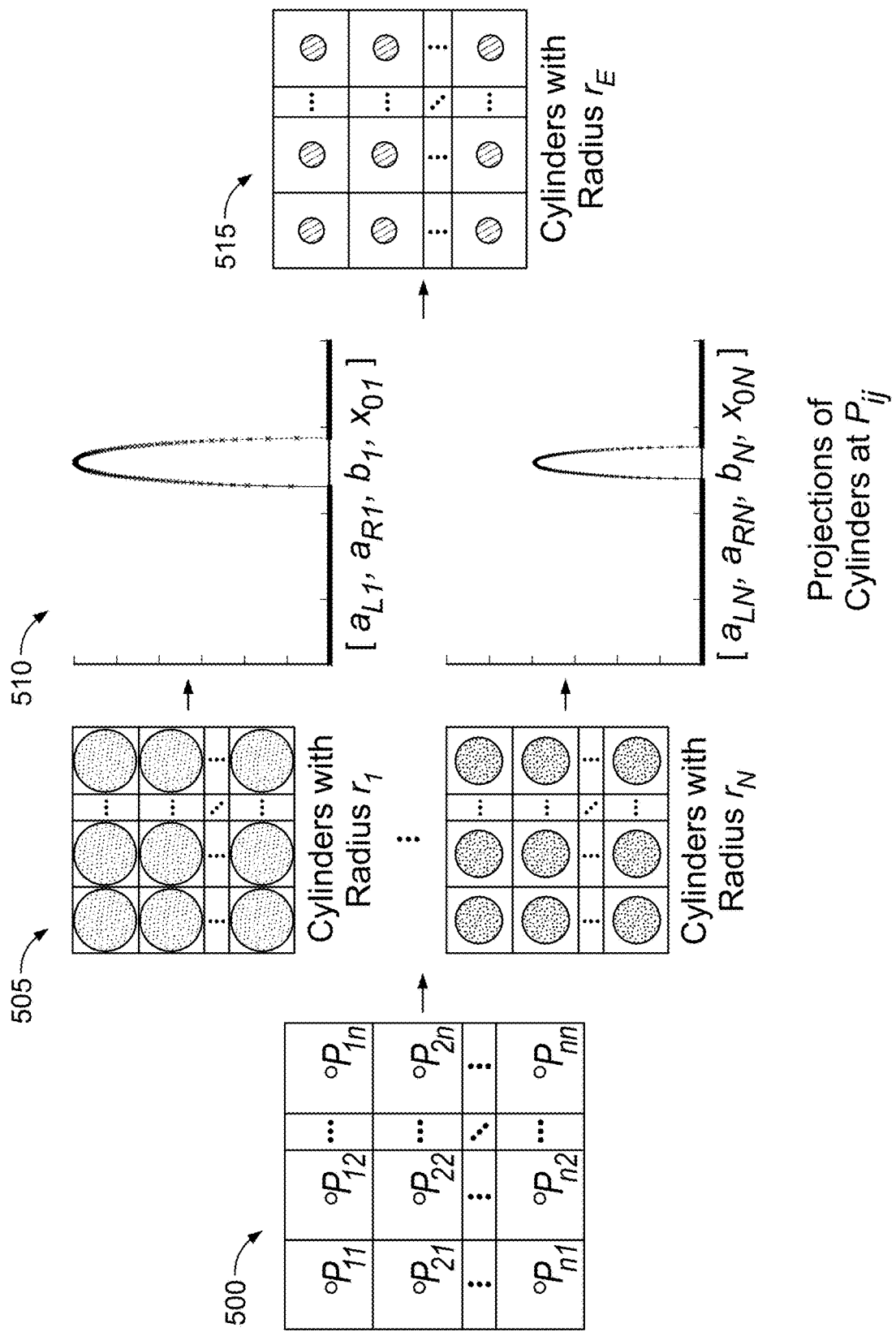
FIG. 5 is a cartoon illustration of steps in an example process for extrapolating the parameters of projection data for a grid of cylinders.

The extrapolation method is illustrated in FIG. 5. The steps of the extrapolation method are as follows:

1. Define (view 500) an n×n grid of point locations $p_{ij}$ in the FOV, i,j=1, 2, . . . , n, $n^2$=N. Each of the N locations represents the center of a respective cylinder to be scanned.
2. Choose a set R of cylinder radii $r_k$, k=1, 2, . . . , N. All radii $r_k$ must be large enough to produce accurate projection data that can be fitted with the ellipse spline.
3. Define a radius $r_E$ equal to the system resolution.
4. For each point $p_{ij}$ in the grid, perform Procedure A and Procedure B, below, to obtain extrapolated parameters $a_{L_{ij}}(r_E)$, $a_{R_{ij}}(r_E)$, $b_{ij}(r_E)$, $x_{0_{ij}}(r_E)$.

Procedure A
  i. Place a single cylinder of radius $r_k$ in the FOV centered at $p_{ij}$.
  ii. Take a single projection of the cylinder (view 505).
  iii. Use the Nelder-Mead method to fit an ellipse spline to the projection. Save the parameters $a_{Lk}$, $a_{Rk}$, $b_k$, $x_{0k}$ that describe the projection. (View 510.)

Figure 6A:
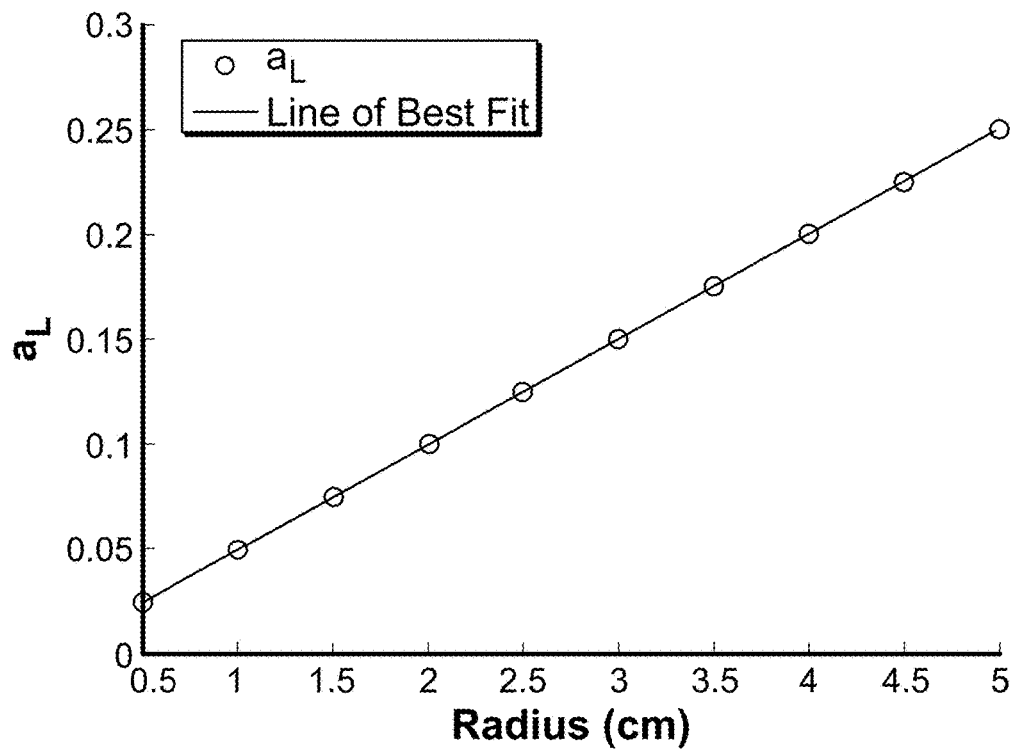
FIGS. 6A and 6B illustrate the extrapolation of projection parameters by graphing parameter value versus radius.
Figure 6B:
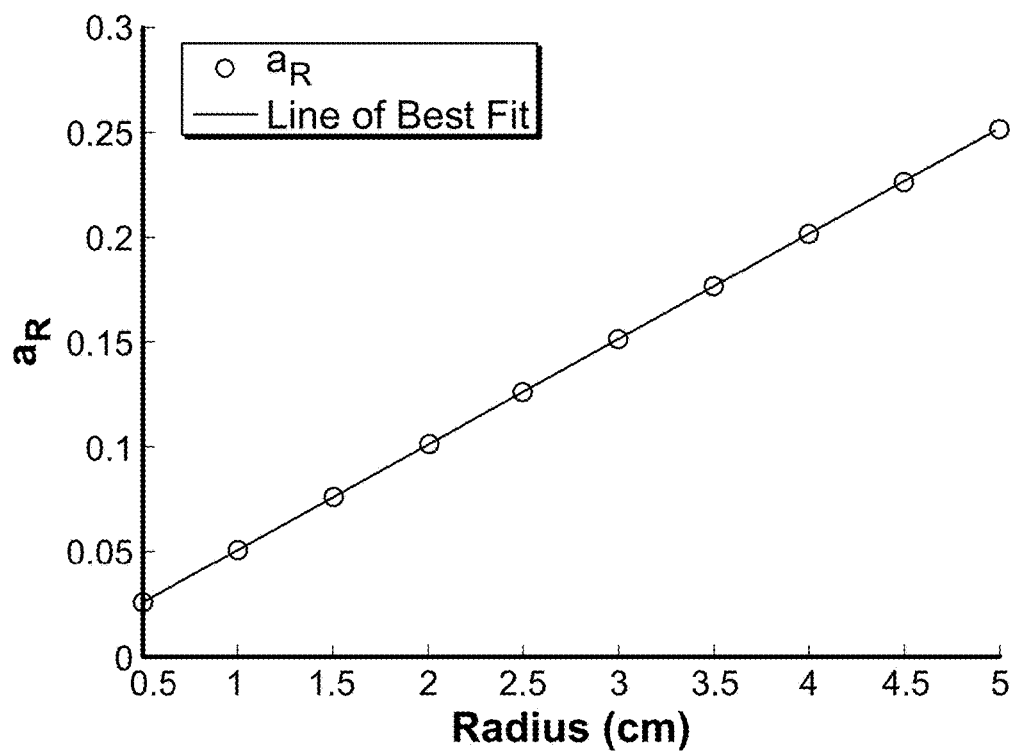
Figure 7A:
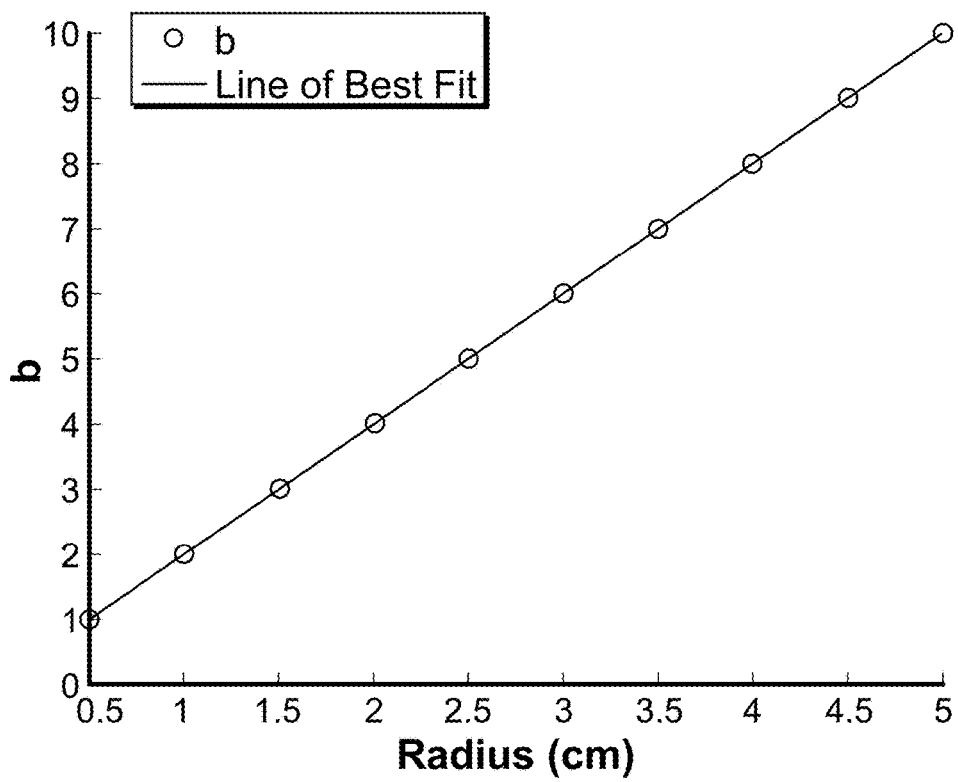
FIGS. 7A and 7B further illustrate the extrapolation of projection parameters by graphing parameter value versus radius.
Figure 7B:
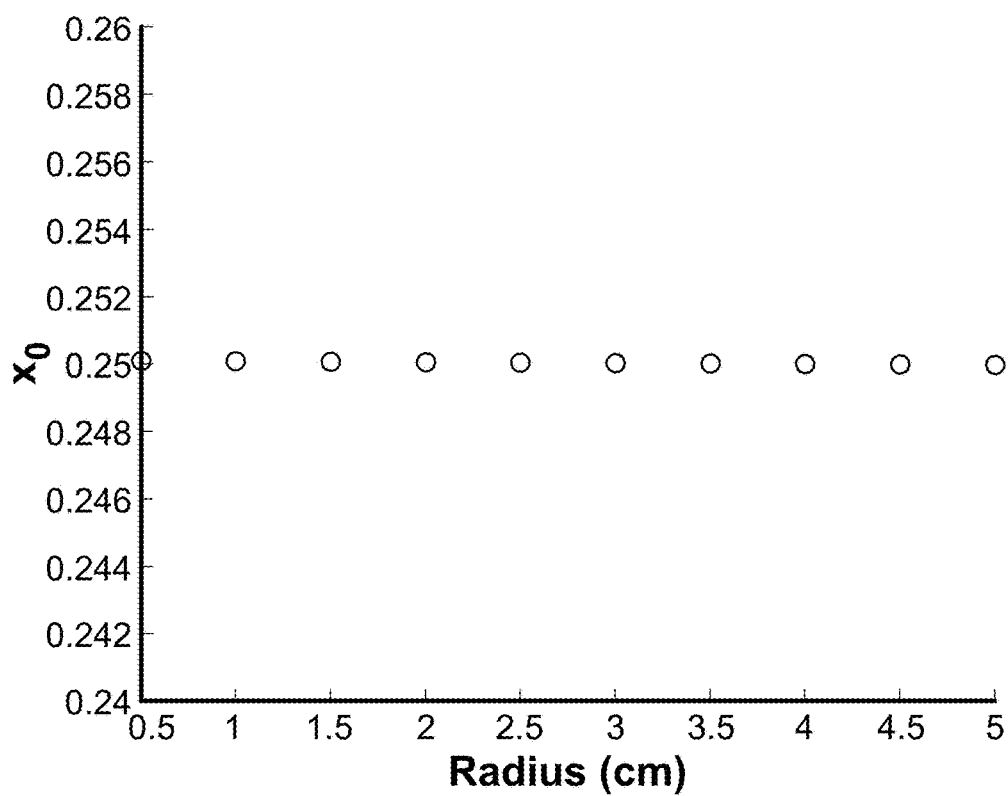

Procedure B (This procedure is predicated on linear variation of the $a_L$, $a_R$, and b parameters with radius, as seen in FIGS. 6A, 6B, and 7A, respectively, and on the variation of the $x_0$ parameter with position only, as seen in FIG. 7B.)
  i. Use the Nelder-Mead method to fit a linear function $a_L(r)$ to the set of coordinate pairs $(a_{Lk}, r_k)$, a linear function $a_R(r)$ to the set of coordinate pairs $(a_{Rk}, r_k)$, and a linear function $b(r)$ to the set of coordinate pairs $(b_k, r_k)$, k=1, 2, . . . , N.
  ii. Extrapolate (view 515) the parameters by evaluating $a_L(r)$ at $r=r_E$, $a_R(r)$ at $r=r_E$, and $b(r)$ at $r=r_E$ to determine $a_L(r_E)$, $a_R(r_E)$, and $b(r_E)$, respectively. Save these values as $a_{L_{ij}}(r_E)$, $a_{R_{ij}}(r_E)$, and $b_{ij}(r_E)$, respectively.
  iii. Take the arithmetic mean of the set of values $x_{0k}$, k=1, 2, . . . , N, and set the result equal to $x_0(r_E)$. Save this value as $x_{0_{ij}}(r_E)$.
  iv. The extrapolated parameters for the cylinder at location $p_{ij}$ are given by $a_{L_{ij}}(r_E)$, $a_{R_{ij}}(r_E)$, $b_{ij}(r_E)$, and $x_{0_{ij}}(r_E)$.
  v. We define $P_{n \times n}$ as the set of all extrapolated parameters $a_{L_{ij}}(r_E)$, $a_{R_{ij}}(r_E)$, $b_{ij}(r_E)$, $x_{0_{ij}}(r_E)$, i, j=1, 2, . . . , n. Store $P_{n \times n}$ in an n×n×4 matrix. (κ=4 is the number of parameters that describe a projection.)

Interpolation of the system operator. Because of the great volume of data, even a single projection is time-consuming to measure. For example, it took up to thirty minutes per projection to acquire H-CT data in our trial runs. As a consequence, it is advantageous to subsample rather than to measure the point response at every voxel in the FOV, and to use an interpolation method to construct the system operator.

We found it unnecessary to interpolate full projections. Instead, it was sufficient to interpolate the parameters (e.g., the four-tuples discussed above) that characterize the fitted projections. Accordingly, the initial data for the interpolation method consisted of the extrapolated parameters discussed above.

Figure 8:
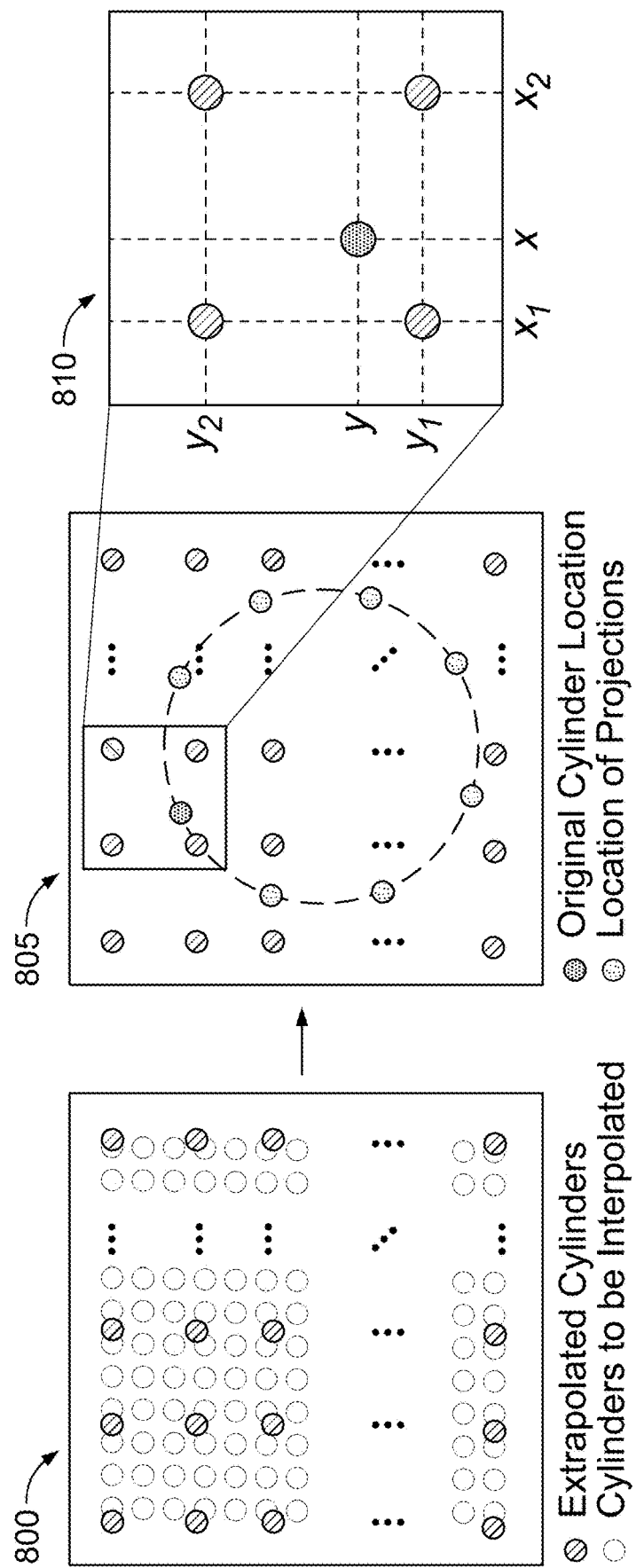
FIG. 8 is a cartoon illustration of steps in an example process for interpolating projection parameters for a grid of cylinders.

The interpolation method is illustrated in FIG. 8.

The interpolation method was performed with the following steps:

1. Define (view 800) an m×m grid of point locations in the FOV, where each location represents the center of a cylinder $C_{ij}$, i,j=1, 2, . . . , m, m≤n.
2. For each cylinder $C_{ij}$, perform the following:
  (a) Determine the number numProj of projections needed for full Nyquist sampling. A full scan of cylinder $C_{ij}$ would consist of numProj projections, each taken at a respective projection angle. As will be seen below, the projections in this set are imputed by interpolating known projection parameters of certain clusters of other cylinders in the m×m grid.
  (b) Compute (view 805) a set of locations $p_k$, k=1, . . . , numProj, in the FOV. Each of these locations corresponds to a respective projection angle $\theta_k$. An imputed cylinder at each location $p_k$ is the image of cylinder $C_{ij}$ under rotation of the FOV by angle $\theta_k$. The imputed projections (as detailed below) of all of these imputed cylinders (plus the original projection of cylinder $C_{ij}$) constitute the full scan, i.e., the full set of projections, of cylinder $C_{ij}$.
  (c) Perform (view 810) the following for each projection location $p_k$:
    i. Identify the four nearest-neighboring points to projection location $p_k$ in the FOV.
    ii. From the respective parameters values in $P_{n \times n}$ for the four neighboring points, perform a bilinear interpolation to estimate the four parameters $a_L$, $a_R$, b, and $x_0$ for the k-th projection of the ij-th cylinder.

3. Store the interpolated parameter values in a numProj× 4×m² matrix $\hat{P}_{m \times m}$. It will be understood that m² corresponds to the number of projected cylinders.

It is noteworthy that the interpolation method described above rests on an assumption that the behavior of the projection system can be treated as linear. This assumption is most valid, hence the interpolations are most accurate, for a multispectral system in which the projection data are collected for individual, spectrally limited, energy bins.

Decompression of the System Operator. In our trials, which are discussed below, we applied the system matrix H to a mathematical representation (as a vector by $\vec{f}$) of an object in the FOV in order to generate an image vector $\vec{g}$, representing a sinogram of the object. We then used the FDK algorithm to reconstruct the object from the sinogram. FDK is a well-known filtered back-projection algorithm that was developed for image reconstruction in cone-beam projection systems. Importantly, image reconstruction by FDK does not require a priori knowledge of the system operator. A faithful reconstruction obtained without a priori knowledge would confirm the validity of our approach to system characterization.

On the other hand, a priori knowledge of the system operator can be of great advantage when it is applied for image reconstruction using iterative reconstruction techniques. In one important application of our approach, a system matrix is generated from calibration measurements, parametrized, and stored in compressed form. For image reconstruction, the system matrix is decompressed and its data are used in an iterative procedure for reconstructing an image from a sinogram.

As explained above, the extrapolated and interpolated parameters describing the point-spread functions are stored in the matrix $\hat{P}_{m \times m}$. These data need to be decompressed in order to recover the system matrix H for use, e.g., in producing the image vector $\vec{g}$ for evaluation.

As will be understood from the discussion above, each column of H corresponds to the stacked projections of one respective cylinder.

The depth (in rows) of one stacked projection is the number n of pixels in the detector. The i'th row within the j'th one of these stacks (i=1, . . . , n) contains the i'th pixel value in the j'th projection of each of the cylinders in sequence. Hence (as will be seen below), the scalar product of such a row with the object vector $\vec{f}$ gives the i'th pixel value in the j'th projection of the object.

As explained above, each projection, hence each stack of n rows of H, is associated with a respective 4-tuple of parameters $a_L$, $a_R$, b, $x_0$. These parameters are invoked in order to perform the decompression and thereby recover the pixel values in the projection of each of the cylinders.

Recall that the process of generating the image vector $\vec{g}$ is represented by $$\vec{g} = H\vec{f},$$

(the additive noise factor $\vec{n}$ is suppressed here) where n is the number of pixels in the detector, m is the number of pixels times the total number of projections, $\vec{f}$ is the discretized n×1 object representation, $\vec{g}$ and $\vec{n}$ have dimensions m×1, and H has dimensions m×n.

Therefore, to decompress H, the stack of n rows of H corresponding to the i'th projection (for all cylinders) is decompressed and multiplied by $\vec{f}$ to produce a stack of n entries of $\vec{g}$ corresponding to the i'th projection and by the same token, the i'th line of the resulting sinogram. To construct the entire sinogram, all rows of H are decompressed, taking them one stack of n rows at a time.

Example 1: Ideal H-CT Data

In a set of numerical trials, we constructed a system matrix H from ideal, analytically generated H-CT data, and we used it to create a sinogram of a (virtual) test object. The sinogram was reconstructed using the FDK algorithm with knowledge of the projection system geometry, but without a priori knowledge of the system matrix or of the object in the FOV. These trials were carried out to test our compression, extrapolation, interpolation, and decompression methods, with the objective of verifying that we could create an ideal system operator that would emulate a real-world system operator.

Figure 9:
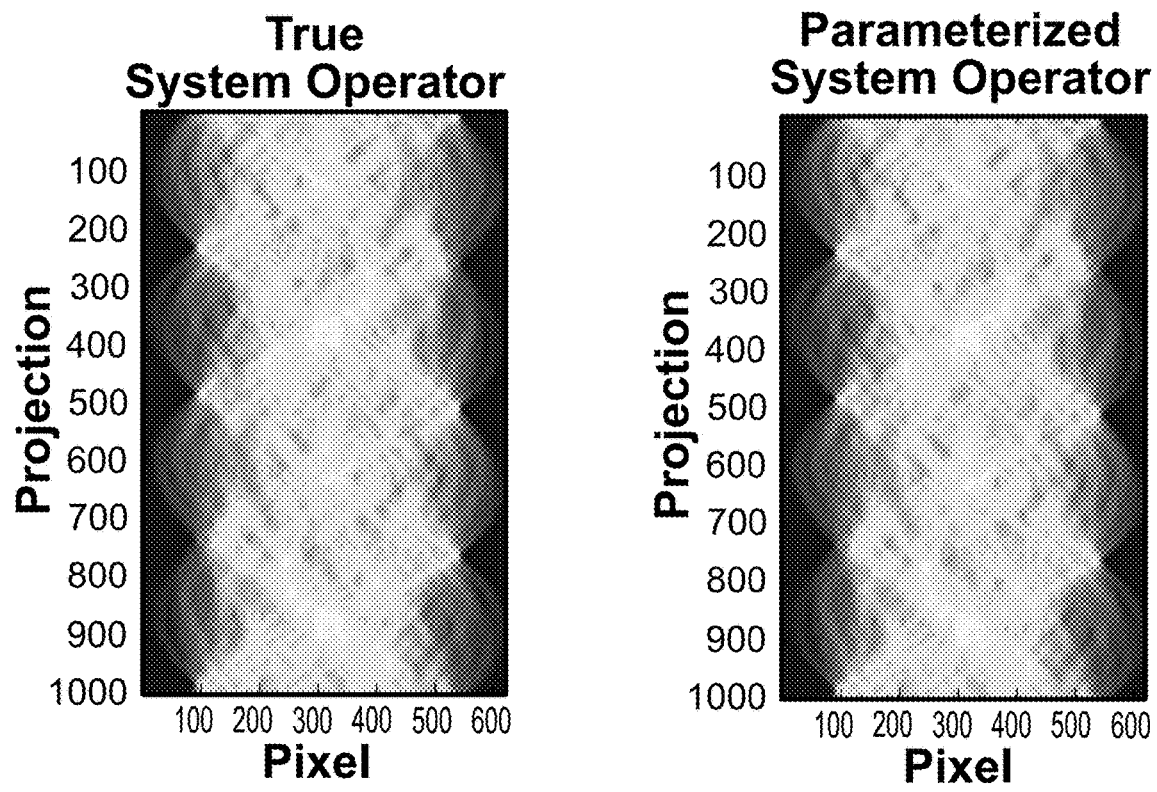
FIG. 9 is a pair of sinograms corresponding to a random object vector f applied to a system operator constructed from a 20×20 sampling of the FOV. The image on the left corresponds to a true system operator with no compression, extrapolation, or interpolation applied. The image on the right, provided for comparison, corresponds to a parameterized and decompressed system operator. Values were calculated using ideal H-CT data.
Figure 10:
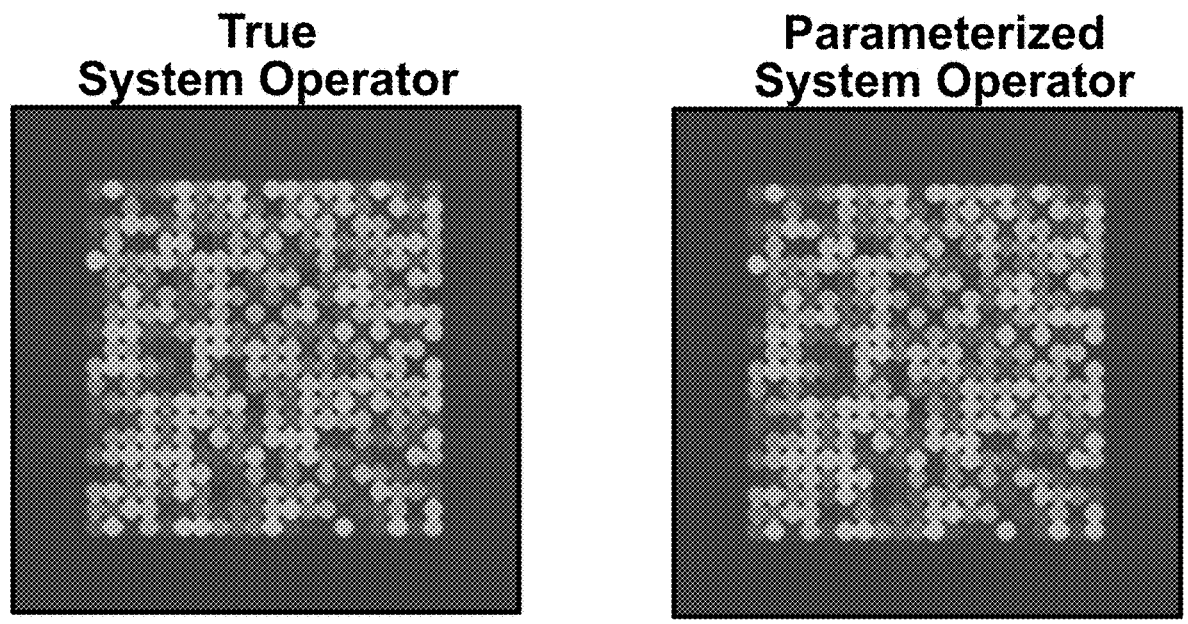
FIG. 10 is a pair of images of the original object as reconstructed from the sinograms of FIG. 9. The image on the left is the reconstruction corresponding to the true system operator. The image on the right is the reconstruction corresponding to the parameterized and decompressed system operator. Values were calculated using ideal H-CT data.

Results of the first trial are shown in FIGS. 9 and 10. We created H from a 20×20 sampling of the FOV with cylinders of radius 0.8 cm. Ideal projection data was calculated analytically for two 10×10 grids of cylinders with radii 3 cm and 1 cm, respectively, and each projection was parameterized.

The parameters in $P_{10 \times 10}$ describing all projections of a 10×10 grid of cylinders with a radius of 0.8 cm were then extrapolated from the parameters corresponding to the cylinders of larger radii. Next, the parameters in $\hat{P}_{20/20}$ for all projections of a 20×20 grid of cylinders with a radius 0.8 cm were interpolated from the extrapolated parameters in $P_{10 \times 10}$. Finally, the interpolated parameters in $\hat{P}_{20 \times 20}$ were decompressed and applied to a random 400×1 object vector $\vec{f}$ to produce the image, given as a sinogram.

FIG. 9, left, shows the sinogram corresponding to the true system operator, with no compression, extrapolation, or interpolation. FIG. 9, right, shows the sinogram corresponding to the parameterized and decompressed system operator.

FIG. 10, left, shows the object reconstruction corresponding to the true system operator. FIG. 10, right, shows the object reconstruction corresponding to parameterized and decompressed system operator.

To test the validity of the results, a true system operator for the ideal system was created by constructing a full H matrix from direct measurements of all projections for a 20×20 grid of cylinders with radius 0.8 cm; no compression, extrapolation, or interpolation was applied to the true system operator. The error was calculated, pixel-by-pixel, by squaring the difference in pixel value between the true system-operator sinogram and the parameterized system operator sinogram. A similar error calculation was performed for the reconstructed images. The mean squared error is shown in Table 1, in units that are a measure of pixel intensity.

In the second trial, we created two system operators, H and $\tilde{H}$. To create H, the parameters in $P_{128 \times 128}$ describing a single projection for each cylinder in a 128×128 grid of cylinders of radius 0.08 cm were extrapolated from two 128×128 grids of cylinders with radii 0.7 cm and 0.5 cm, respectively. The parameters in $\hat{P}_{128 \times 128}$ for all projections of a 128×128 grid of cylinders with radius 0.08 cm were interpolated from the extrapolated parameters in $P_{128 \times 128}$.

To create $\tilde{H}$, the parameters in $P_{64 \times 64}$ describing a single projection for each cylinder in a 64×64 grid of cylinders of radius 0.08 cm were extrapolated from two 64×64 grids of cylinders with radii 0.7 cm and 0.5 cm, respectively. The parameters $\hat{P}_{128 \times 128}$ for all projections of a 128×128 grid of cylinders with radius 0.08 cm were interpolated from the extrapolated parameters in $P_{64 \times 64}$.

Figure 11:
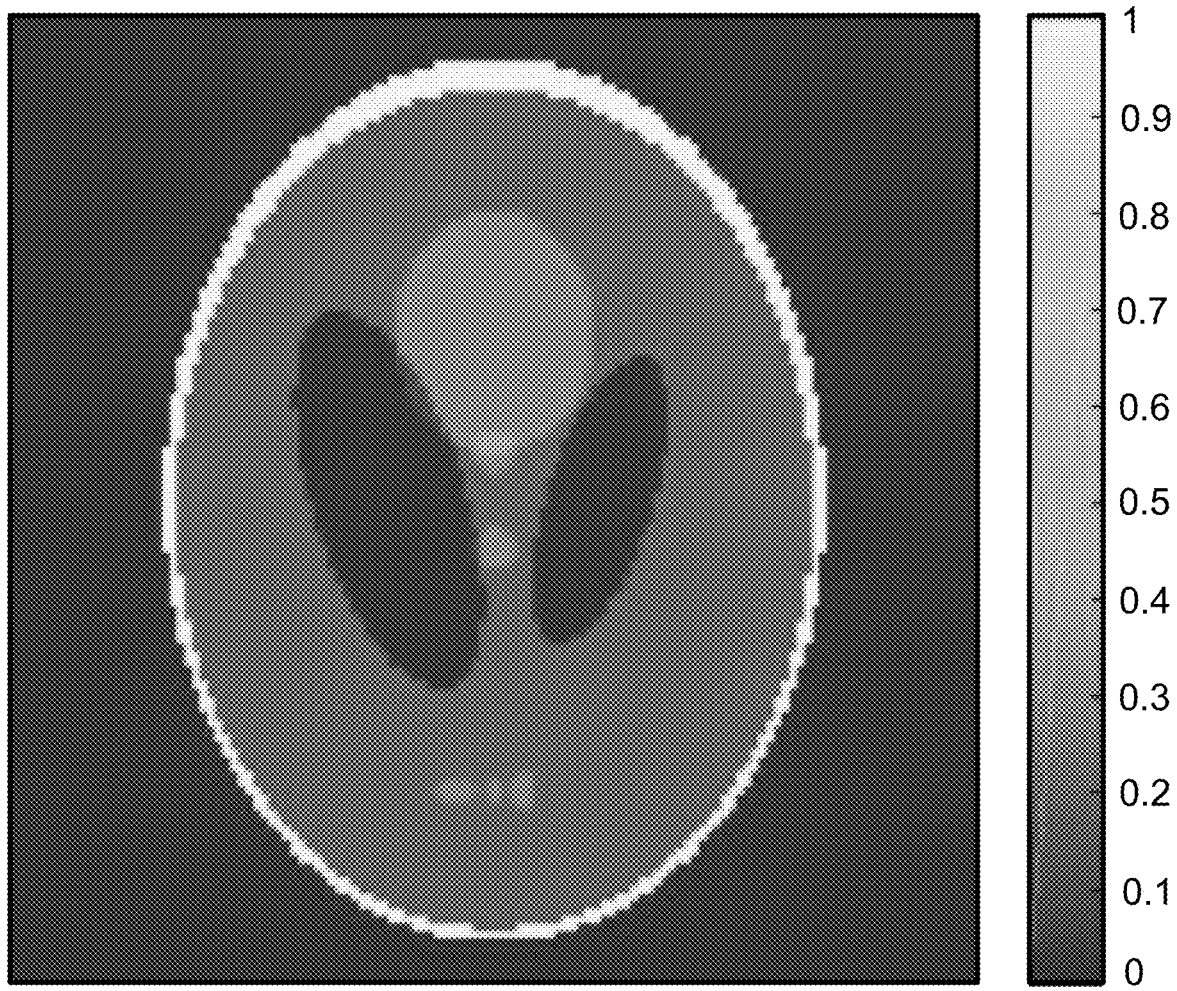
FIG. 11 is an image of the numerically defined Shepp-Logan phantom that was used in some of the trials reported here.

For both H and $\tilde{H}$, the interpolated parameters in $\hat{P}_{128 \times 128}$ and in $\hat{\tilde{P}}_{128 \times 128}$, respectively, were decompressed and applied to $\vec{f}$, a flattened Shepp-Logan phantom given as a 16384×1 vector, shown in FIG. 11.

Figure 12:
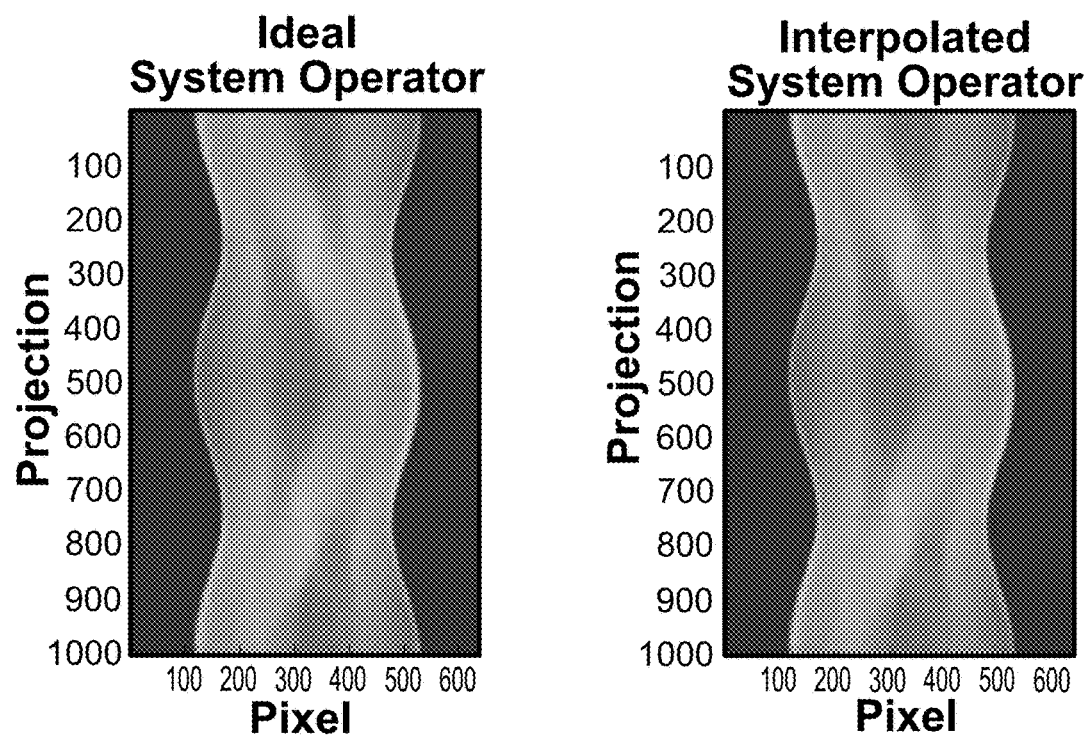
FIG. 12 is a pair of sinograms obtained by applying the Shepp-Logan phantom of FIG. 11 (in flattened form) to a system operator constructed from a 128×128 sampling of the FOV. The sinogram on the left corresponds to an ideal system operator. The sinogram on the right corresponds to an interpolated system operator. Values were calculated using ideal H-CT data.

FIG. 12, left, shows the resulting sinogram corresponding to the "ideal" system operator constructed on the basis of $\hat{P}_{128 \times 128}$. FIG. 12, right, shows the resulting sinogram corresponding to the "interpolated" system operator constructed on the basis of $\hat{\tilde{P}}_{128 \times 128}$.

Figure 13:
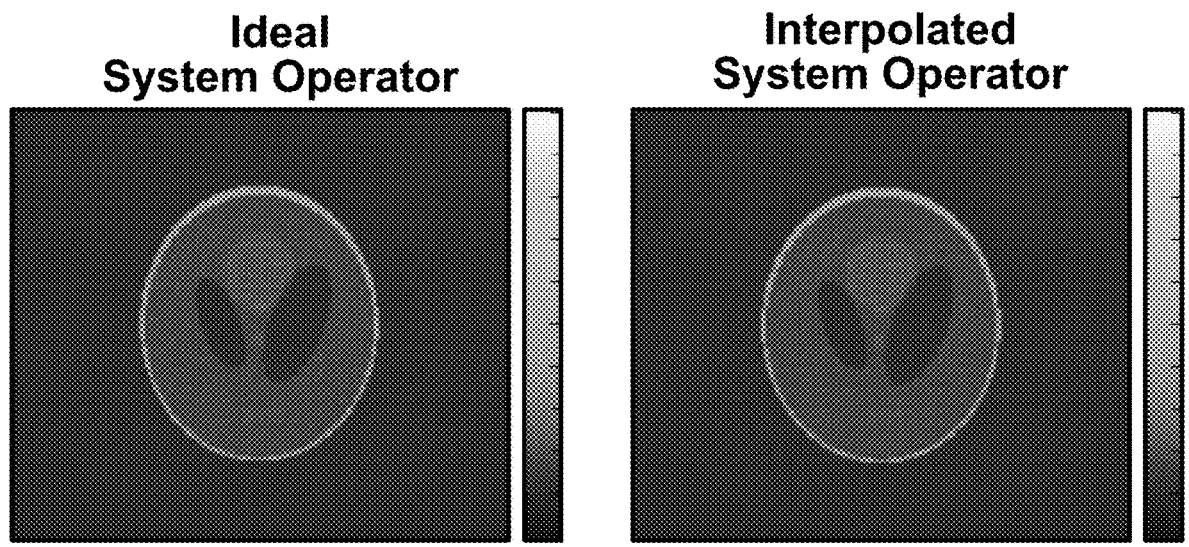
FIG. 13 is a pair of images of the original Shepp-Logan phantom as reconstructed from the sinograms of FIG. 12. The image on the left is the reconstruction corresponding to the ideal system operator. The image on the right is the reconstruction corresponding to the interpolated system operator. Values were calculated using ideal H-CT data.

FIG. 13, left, shows the object reconstruction corresponding to the ideal system operator. FIG. 13, right, shows the object reconstruction corresponding to the interpolated system operator. The mean squared error for the difference between the reconstructions based, respectively, on the ideal and interpolated system operators is shown in Table 2, in units that are a measure of pixel intensity.

TABLE 1

Error, 20 × 20 Sampling, Ideal Data

| Image | Mean Squared Error | Std. Deviation |
|---|---|---|
| Sinograms | $5.99 \times 10^{-5}$ | $3.40 \times 10^{-4}$ |
| Reconstructions | $2.98 \times 10^{-8}$ | $1.22 \times 10^{-7}$ |

TABLE 2

Error, 128 × 128 Sampling, Ideal Data

| Image | Mean Squared Error | Std. Deviation |
|---|---|---|
| Sinograms | $1.34 \times 10^{-8}$ | $2.20 \times 10^{-7}$ |
| Reconstructions | $4.55 \times 10^{-12}$ | $1.25 \times 10^{-11}$ |

Example 2: Simulated H-CT Data

To more closely emulate a real-world system, we performed a trial using H-CT data generated with the PHITS simulation tool, which included noise. To match our laboratory H-CT system, which has a pixel resolution of 0.08 cm, the system operators created with PHITS data also used a sampling of cylinders with radius 0.08 cm.

The trial was performed with the same radii and number of cylinders as the second trial described above in Example 1. Two PHITS simulations were run to collect the data used in the extrapolation. For each simulation, a 128×128 grid of copper cylinders was distributed in the FOV, and one projection was taken for each cylinder. The cylinders in the first simulation had radii of 0.7 cm, and the cylinders in the second simulation had radii of 0.5 cm. The PHITS data was used to extrapolate the parameters in $P_{128 \times 128}$ describing a 128×128 grid of cylinders with radii 0.08 cm.

Due to the noisy nature of the PHITS data, additional pre-processing was required before interpolating the parameters. Outliers in $P_{128 \times 128}$ were detected and replaced with a cubic spline interpolation of neighboring points.

As in the second trial described above in Example 1, two system operators were created based on the PHITS data: "Ideal" system operator H and "interpolated" system operator $\tilde{H}$. H was constructed by interpolating all projections of a 128×128 grid of cylinders of radius 0.08 cm based on the extrapolated parameters in $P_{128 \times 128}$. To create $\tilde{H}$, a 64×64 subset of $P_{128 \times 128}$ was taken to create a 64×64 set of extrapolated parameters, denominated $P_{64\times64}$. We constructed $\tilde{H}$ constructed by interpolating all projections of a 128×128 grid of cylinders of radius 0.08 cm based on the extrapolated parameters in $P_{64\times64}$.

As in the trial described above in Example 1, a flattened Shepp-Logan phantom, given as a 16384×1 vector, was chosen as $\vec{f}$ and multiplied by H and by $\tilde{H}$, respectively.

Figure 14:
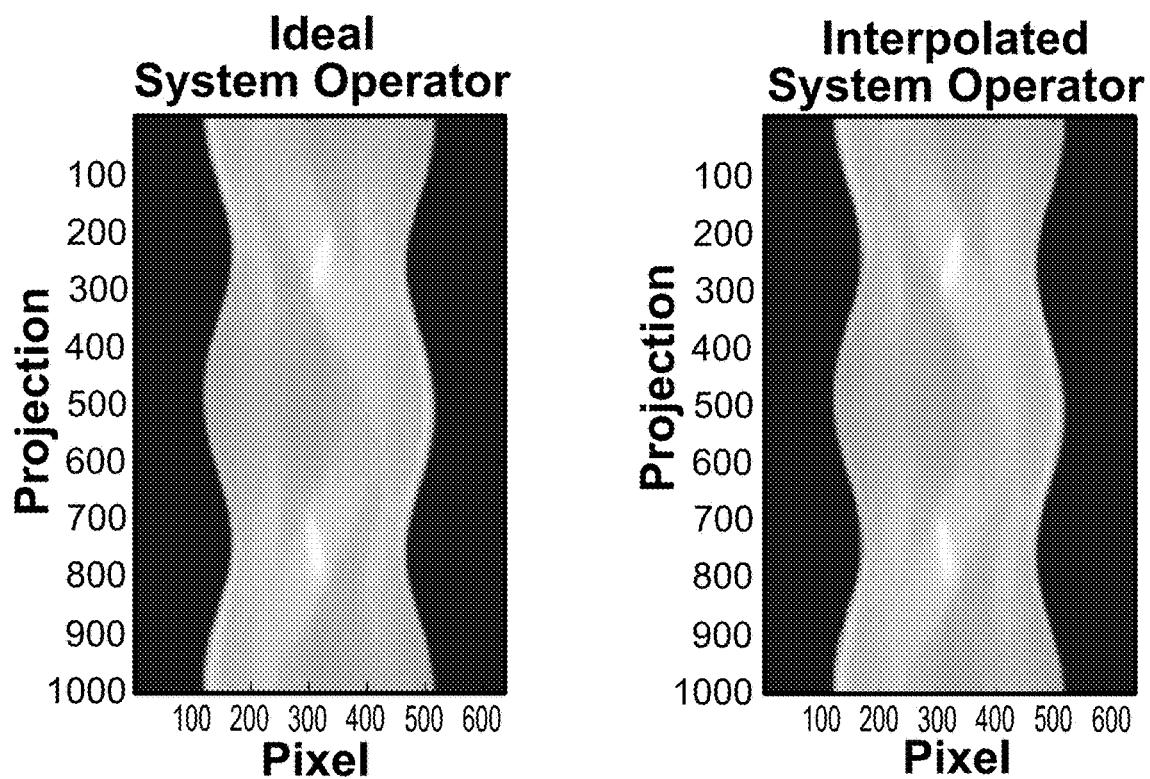
FIG. 14 is a pair of sinograms obtained by applying the Shepp-Logan phantom of FIG. 11 (in flattened form) to a system operator constructed from a 128×128 sampling of the FOV, using simulated H-CT data. The sinogram on the left corresponds to a system operator constructed based on an ideal system operator. The sinogram on the right corresponds to an interpolated system operator.

FIG. 14, left, shows the resulting sinogram corresponding to the ideal system operator. FIG. 14, right, shows the resulting sinogram corresponding to the interpolated system operator.

Figure 15:
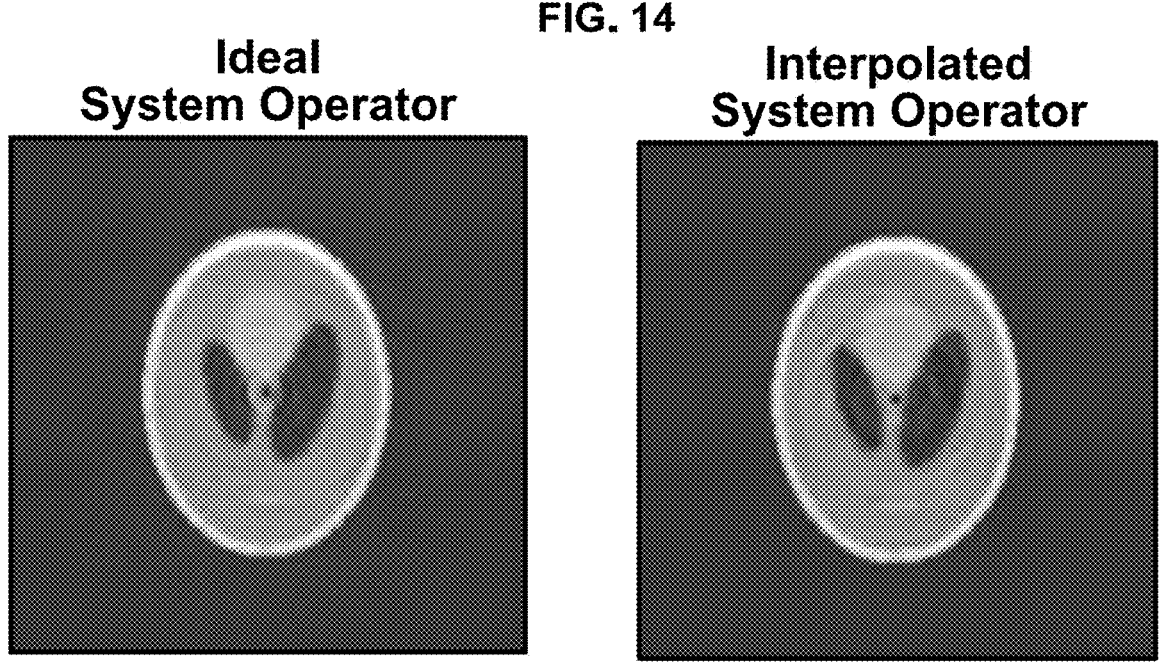
FIG. 15 is a pair of images of the original Shepp-Logan phantom as reconstructed from the sinograms of FIG. 14. The image on the left corresponds to the ideal system operator. The image on the right corresponds to the interpolated system operator. Values were calculated using simulated H-CT data.

FIG. 15, left, shows the image reconstruction corresponding to the ideal system operator. FIG. 15, right, shows the image reconstruction corresponding to the interpolated system operator.

The mean squared error for the difference between the reconstructions based, respectively, on the ideal and interpolated system operators is shown in Table 3, in units that are a measure of pixel intensity. The values listed in Table 3 are scaled by attenuation value, and hence are not directly comparable with the values listed in the preceding tables.

TABLE 3

| Error, 128 × 128 Sampling, Simulated Data | | |
|---|---|---|
| Image | Mean Squared Error | Std. Deviation |
| Sinograms | 4.74 | 10.7 |
| Reconstructions | $1.20 \times 10^{-3}$ | $4.40 \times 10^{-3}$ |

Example 3: Image Reconstruction Using a Priori System Information

We performed trials to assess whether our compressed system operator could be used as a surrogate representation of the imaging system. Our measure of success was whether a 128×128 voxel Shepp-Logan phantom could be accurately reconstructed in a reasonable amount of time from a numerically generated sinogram $\vec{g}$, using an iterative algorithm in which the compressed system matrix provides the a priori system information.

The iterative algorithm that we chose was the Maximum-Likelihood Expectation-Maximization (MLEM) reconstruction algorithm. The MLEM algorithm is given by:

$$\hat{f}_j^{n+1} = \frac{\hat{f}_j^n}{\sum_i H_{ij}} \sum_i \frac{g_i}{\sum_k H_{ik}\hat{f}_k^n},$$

where n is the iteration number, $\hat{f}_j^n$ is the value of the reconstructed image at pixel j for the n'th iteration, i is the pixel number in the sinogram $\vec{g}$, and $H_{ij}$ is the system matrix entry at row i, column j.

To apply the above equation, it is necessary to decompress the compressed system operator each time one of its entries needs to be extracted. Although the decompression can be computationally intensive, it is not difficult to perform efficiently on a massively parallel computing environment such as a graphics processor. Thus, for example, our implementation was developed in CUDA and performed on a Nvidia Titan V graphics processing unit (GPU). CUDA is a Nvidia programming language that allows for computation on Nvidia brand GPUs.

Figure 16:
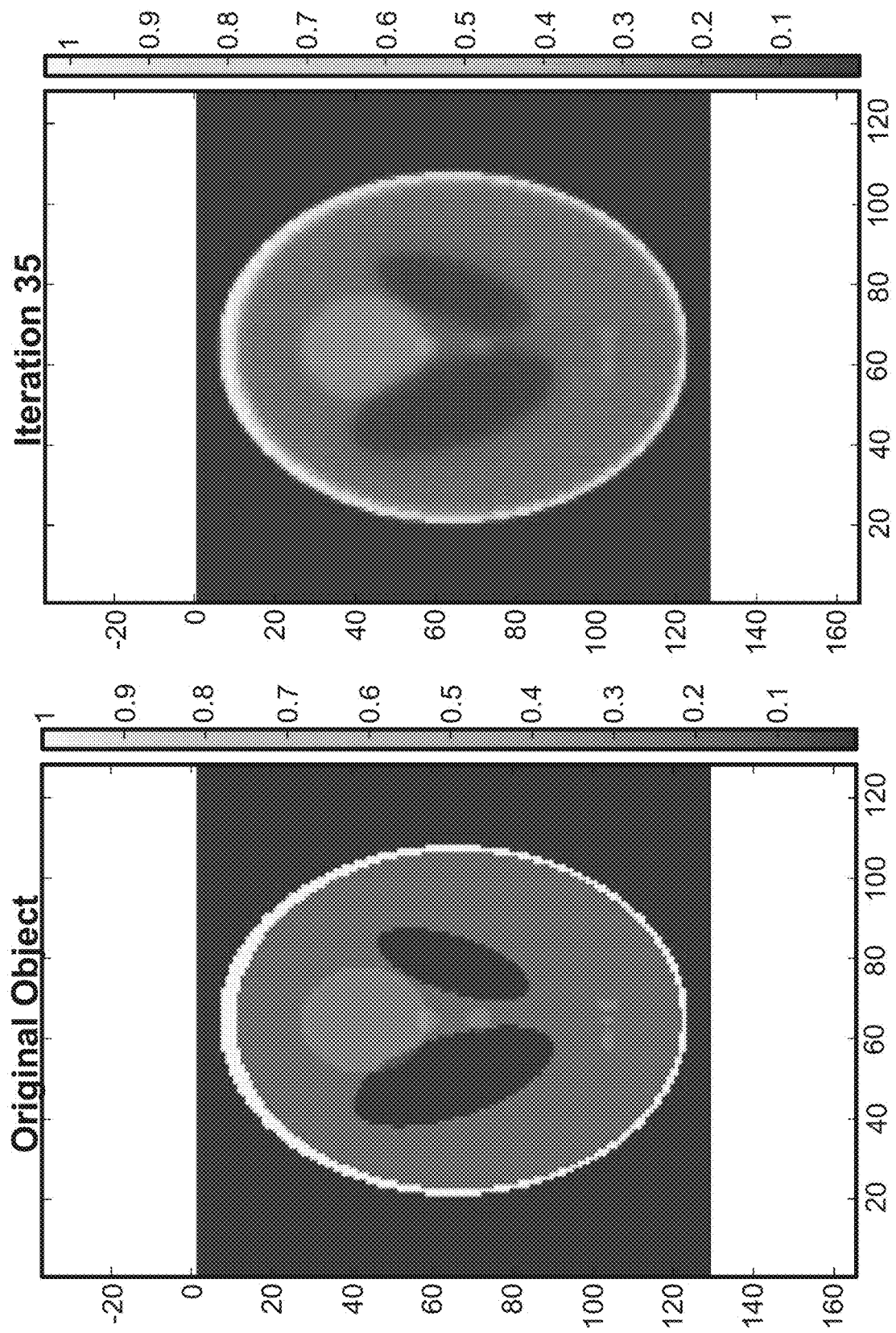
FIG. 16 provides a comparison between the original 128×128 voxel Shepp-Logan phantom (shown on the left), and an image of the phantom that was reconstructed in 35 iterations of the MLEM algorithm (shown on the right).

FIG. 16 shows, side-by-side, the original 128×128 voxel Shepp-Logan phantom (left) shows a reconstruction that we performed using the ellipse-spline compression scheme described above (right). The reconstruction required approximately 72 hours of computation time.

It is evident from the figure that our compressed system operator is useful for image reconstruction. We believe it also has potential for other applications such as forward projection to simulate synthetic images that could be produced by the modeled imaging system.

We claim:

1. A calibration method for an x-ray computerized tomography system, comprising:
   measuring at least one point spread function (PSF) at each of a plurality of points;
   compressing each PSF; and
   in one or more storing operations, storing the compressed PSFs in a computer-accessible storage medium, wherein:
   the PSF measurements are made in a grid of calibration points in a field of view (FOV) of the system;
   the measuring step comprises positioning an absorber at each of the calibration points and taking an x-ray projection at least once at each said absorber position; and
   at each calibration point of the grid, respective PSFs are measured in a plurality of x-ray energy bins;
   wherein compressing each PSF comprises fitting each PSF to an ellipse spline.

2. The method of claim 1, wherein the measuring step comprises performing a scan at each calibration point, each scan comprising multiple x-ray projections taken over a range of projection angles.

3. The method of claim 1, wherein the measuring of a PSF comprises projecting two or more absorbers having different radii so as to generate a graduated set of two or more respective projections, and wherein the compressing of a PSF comprises extrapolating parameter values from its graduated set of projections.

4. The method of claim 1, further comprising calculating imputed PSFs for a plurality of points in the FOV that are additional to the calibration points by interpolation of measured PSFs, and wherein the one or more storing operations comprise storing the imputed PSFs in compressed form.

5. The method of claim 1, wherein:
   the one or more storing operations comprise storing respective scans for multiple points in the FOV;
   each scan comprises multiple projections of an absorber taken at a fixed absorber position but at multiple projection angles; and
   storing a scan comprises storing a compressed PSF for each respective projection angle.

6. The method of claim 5, further comprising computing imputed PSFs for at least some points in the FOV by interpolation of measured PSFs, and wherein at least some of the stored scans include imputed PSFs.

7. The method of claim 1, wherein the compressed PSFs are stored in a matrix of entries arranged in rows and columns, and wherein each entry corresponds to a vector of parameter values representing a respective compressed PSF.

8. The method of claim 1, wherein:
   the system has a spatial resolution;
   the one or more storing operations comprise storing at least one compressed PSF for every point in a voxelization grid within the FOV; and
   the voxelization grid has a pitch of at least the system spatial resolution.

9. A calibration method for an x-ray computerized tomography system, comprising:
measuring at least one point spread function (PSF) at each of a plurality of points;
compressing each PSF; and
in one or more storing operations, storing the compressed PSFs in a computer-accessible storage medium, wherein:
the PSF measurements are made in a grid of calibration points in a field of view (FOV) of the system;
the measuring step comprises positioning an absorber at each of the calibration points and taking an x-ray projection at least once at each said absorber position; and
at each calibration point of the grid, respective PSFs are measured in a plurality of x-ray energy bins;
wherein compressing each PSF comprises representing each PSF by a vector of parameters including a scale parameter, a translational parameter, and at least one shape parameter.

10. The method of claim 9, wherein the measuring of a PSF comprises projecting two or more absorbers having different radii so as to generate a graduated set of two or more respective projections, and wherein the compressing of a PSF comprises extrapolating parameter values from its graduated set of projections.

11. A calibration method for an x-ray computerized tomography system, comprising:
measuring at least one point spread function (PSF) at each of a plurality of points;
compressing each PSF; and
in one or more storing operations, storing the compressed PSFs in a computer-accessible storage medium, wherein:
the PSF measurements are made in a grid of calibration points in a field of view (FOV) of the system;
the measuring step comprises positioning an absorber at each of the calibration points and taking an x-ray projection at least once at each said absorber position; and
each compressed PSF consists of at most four parameters of a spline fit.

12. The method of claim 11, wherein compressing each PSF comprises fitting each PSF to an ellipse spline.

13. The method of claim 11, wherein compressing each PSF comprises representing each PSF by a vector of parameters including a scale parameter, a translational parameter, and at least one shape parameter.

14. The method of claim 11, wherein the measuring step comprises performing a scan at each calibration point, each scan comprising multiple x-ray projections taken over a range of projection angles.

15. The method of claim 11, wherein the measuring of a PSF comprises projecting two or more absorbers having different radii so as to generate a graduated set of two or more respective projections, and wherein the compressing of a PSF comprises extrapolating parameter values from its graduated set of projections.

16. The method of claim 11, further comprising calculating imputed PSFs for a plurality of points in the FOV that are additional to the calibration points by interpolation of measured PSFs, and wherein the one or more storing operations comprise storing the imputed PSFs in compressed form.

17. The method of claim 11, wherein:
the one or more storing operations comprise storing respective scans for multiple points in the FOV;
each scan comprises multiple projections of an absorber taken at a fixed absorber position but at multiple projection angles; and
storing a scan comprises storing a compressed PSF for each respective projection angle.

18. The method of claim 17, further comprising computing imputed PSFs for at least some points in the FOV by interpolation of measured PSFs, and wherein at least some of the stored scans include imputed PSFs.

19. The method of claim 11, wherein the compressed PSFs are stored in a matrix of entries arranged in rows and columns, and wherein each entry corresponds to a vector of parameter values representing a respective compressed PSF.

20. The method of claim 11, wherein:
the system has a spatial resolution;
the one or more storing operations comprise storing at least one compressed PSF for every point in a voxelization grid within the FOV; and
the voxelization grid has a pitch of at least the system spatial resolution.

21. A calibration method for an x-ray computerized tomography system, comprising:
measuring at least one point spread function (PSF) at each of a plurality of points;
compressing each PSF; and
in one or more storing operations, storing the compressed PSFs in a computer-accessible storage medium, wherein:
the PSF measurements are made in a grid of calibration points in a field of view (FOV) of the system;
the measuring step comprises positioning an absorber at each of the calibration points and taking an x-ray projection at least once at each said absorber position;
the measuring of a PSF comprises projecting two or more absorbers having different radii so as to generate a graduated set of two or more respective projections; and
the compressing of a PSF comprises extrapolating parameter values from its graduated set of projections.

* * * * *